United States Patent
Hall et al.

(10) Patent No.: US 10,768,172 B2
(45) Date of Patent: *Sep. 8, 2020

(54) ANTI-BED BUG MONOCLONAL ANTIBODIES AND METHODS OF MAKING AND USES THEREOF

(71) Applicant: Redcoat Solutions, Inc., Harrisonburg, VA (US)

(72) Inventors: William John Hall, Harrisonburg, VA (US); Min Wang, San Diego, CA (US)

(73) Assignee: Redcoat Solutions, Inc., Harrisonburg, VA (US)

( * ) Notice: Subject to any disclaimer, the term of this patent is extended or adjusted under 35 U.S.C. 154(b) by 371 days.

This patent is subject to a terminal disclaimer.

(21) Appl. No.: 15/331,632

(22) Filed: Oct. 21, 2016

(65) Prior Publication Data

US 2017/0137501 A1 May 18, 2017

Related U.S. Application Data

(60) Provisional application No. 62/244,189, filed on Oct. 21, 2015.

(51) Int. Cl.
| | |
|---|---|
| *G01N 33/53* | (2006.01) |
| *C07K 16/00* | (2006.01) |
| *C12N 5/16* | (2006.01) |
| *C12N 5/12* | (2006.01) |
| *G01N 33/577* | (2006.01) |
| *G01N 33/558* | (2006.01) |
| *B01J 13/00* | (2006.01) |

(52) U.S. Cl.
CPC ........ *G01N 33/5308* (2013.01); *C07K 16/00* (2013.01); *C12N 5/12* (2013.01); *C12N 5/163* (2013.01); *G01N 33/577* (2013.01); *B01J 13/0043* (2013.01); *B22F 2301/255* (2013.01); *B22F 2304/054* (2013.01); *B22F 2304/056* (2013.01); *C07K 2317/14* (2013.01); *C07K 2317/56* (2013.01); *C07K 2317/565* (2013.01); *G01N 33/558* (2013.01); *G01N 2333/43552* (2013.01)

(58) Field of Classification Search
None
See application file for complete search history.

(56) References Cited

U.S. PATENT DOCUMENTS

| | | |
|---|---|---|
| 6,319,676 B1 | 11/2001 | Nazareth et al. |
| 7,129,053 B1 | 10/2006 | Reiter et al. |
| 7,214,542 B2 | 5/2007 | Hutchinson |
| 7,220,597 B2 | 5/2007 | Zin et al. |
| 7,482,128 B2 | 6/2009 | Jensen et al. |
| 7,591,099 B2 | 9/2009 | Lang et al. |
| 7,727,734 B1 | 6/2010 | Smith |
| 7,743,552 B2 | 6/2010 | Borth et al. |
| 8,375,626 B2 | 2/2013 | Borth et al. |
| 8,435,461 B2 | 5/2013 | Kirby et al. |
| 8,460,890 B2 | 6/2013 | Smith |
| 8,551,968 B2 | 10/2013 | Refaeli et al. |
| 8,606,528 B2 | 12/2013 | Sharrock |
| 8,617,486 B2 | 12/2013 | Kirby et al. |
| 8,984,084 B2 | 3/2015 | Borth et al. |
| 9,188,583 B2 | 11/2015 | Vaidyanathan et al. |
| 9,458,512 B2 | 10/2016 | Colaizzi et al. |
| 9,500,643 B2 | 11/2016 | Vaidyanathan et al. |
| 9,549,542 B2 | 1/2017 | Cain |
| 10,045,520 B2 | 8/2018 | Carver et al. |
| 10,264,776 B2 | 4/2019 | Borth et al. |
| 2008/0311002 A1 | 12/2008 | Kirby et al. |
| 2009/0155921 A1 | 6/2009 | Lu et al. |
| 2010/0120061 A1 | 5/2010 | Badwan et al. |
| 2010/0212213 A1 | 8/2010 | Hope et al. |
| 2010/0233731 A1 | 9/2010 | Smith |
| 2010/0273177 A1 | 10/2010 | Piasio et al. |
| 2011/0044936 A1 | 2/2011 | Black et al. |
| 2011/0289824 A1 | 12/2011 | Wu et al. |
| 2012/0072125 A1 | 3/2012 | Sharrock et al. |
| 2013/0208114 A1 | 8/2013 | Balsam |
| 2014/0011190 A1 | 1/2014 | Parviainen et al. |
| 2014/0234949 A1 | 8/2014 | Wasson et al. |
| 2015/0064727 A1 | 3/2015 | Vaidyanathan et al. |
| 2015/0301031 A1 | 10/2015 | Zin et al. |

(Continued)

FOREIGN PATENT DOCUMENTS

| | | |
|---|---|---|
| AU | 2013200548 B2 | 2/2013 |
| WO | WO 99/64863 A1 | 12/1999 |
| WO | WO 2013/096817 A2 | 6/2013 |

(Continued)

OTHER PUBLICATIONS

Rudikoff et al. "Single amino acid substitution altering antigen-binding specificity" Proc Natl Acad Sci USA 1982 vol. 79 pp. 1979-1983.*

Pascalis et al. "Grafting of "abbreviated" complementarity-determining regions containing specificity-determining residues essential for ligand contact to engineer a less immunogenic humanized monoclonal antibody", The Journal of Immunology (2002) 169, 3076-3084.*

Casset et al. "A peptide mimetic of an anti-CD4 monoclonal antibody by rational design" (2003) BBRC 307, 198-205.*

Van Regenmortel "Molecular dissection of protein antigens and the prediction of epitopes", Chapter 1 in: Laboratory Techniques in Biochemistry and Molecular Biology vol. 19, 1988, pp. 1-39.*

(Continued)

*Primary Examiner* — Christine Foster
(74) *Attorney, Agent, or Firm* — Sterne, Kessler, Goldstein & Fox P.L.L.C.

(57) ABSTRACT

The present disclosure provides anti-bed bug monoclonal antibodies and antigen-binding fragments thereof as well as compositions and kits comprising the same. The present disclosure also provides methods of making monoclonal antibodies and antigen-binding fragments thereof and methods of using the same to detect bed bugs.

22 Claims, 20 Drawing Sheets

(56) References Cited

U.S. PATENT DOCUMENTS

2017/0115301 A1* 4/2017 Hall ...................... C07K 16/18

FOREIGN PATENT DOCUMENTS

| WO | WO 2013/130613 A1 | 9/2013 |
|---|---|---|
| WO | WO-2017-037126 A1 | 3/2017 |
| WO | WO-2017-070594 A1 | 4/2017 |

OTHER PUBLICATIONS

Arkle, S., et al., "Antibody Detection by ELISA in Chicken Infested with *Dermanyssus gallinae*," *Epidémiol et santé anim* 48:15-19, Maisons-Alfort, France (2005).

Blow, J.A., et al., "Stercorarial Shedding and Transtadial Transmission of Hepatitis B Virus by Common Bed Bugs (Hemiptera: Cimicidae)" *J. Med. Entomol.* 38: 694-700, Entomological Society of America, United States (2001).

Eom, I.Y., et al., "Simultaneous sampling and analysis of indoor air infested with *Cimex lectularius* L. (Hemiptera: Cimicidae) by solid phase microextraction, thin film microextraction and needle trap device," *Anal Chim Acta* 716: 2-10, Elsevier B.V., The Netherlands (2012).

Lowe, C.F. and Romnney M.G., "Bedbugs as Vectors for Drug-Resistant Bacteria" *Emerg. infect. Dis.* 17:1132-1134, National Center for Infectious Diseases, United States (2011).

Mankin, R.W., et al., "Acoustic Indicators for Targeted Detection of Stored Product and Urban Insect Pests by Inexpensive Infrared, Acoustic, and Vibrational Detection of Movement," *J. Econ. Entomol.* 103: 1636-1646, Entomological Society of America, United States (2010).

Prudencio, C.R., et al., "Recombinant peptides as new immunogens for the control of the bovine tick, *Rhipicephalus (Boophilus)microplus*," Vet Parasitol 172(1-2):122-131, Elsevier B.V., Netherlands (2010).

Szalanski, A.L., et al., "Multiplex Polymerase Chain Reaction Diagnostics of Bed Bug (Hemiptera: Cimicidae)," *J. Med. Entomol.* 48: 937-940, Entomological Society of America, United States (2011).

Vaidyanathan, R., et al., "Review Article: Bed Bug Detection: Current Technologies and Future Directions," *Am. J. Trpp. Med. Hyg.* 88(4), 2013, pp. 619-625, United States (2013).

Wong, M., et al., Strategies for Housing Authorities and Other Lower-Income Housing Providers to Control Bed Bugs, *Journal of Housing & Community Development* vol. 70 issue 3, pp. 20-28, United States (2013).

International Search Report for International Patent Application No. PCT/US2013/028028, Korean Intellectual Property Office, Republic of Korea, dated Jun. 3, 2013, 3 pages.

Written Opinion of the International Searching Authority for International Patent Application No. PCT/US2013/028028, Korean Intellectual Property Office, Republic of Korea, dated Jun. 3, 2013, 5 pages.

Non-final Office Action dated Dec. 19, 2014, in U.S. Appl. No. 14/382,113, 371(c) date: Aug. 29, 2014.

Final Office Action dated Apr. 6, 2015, in U.S. Appl. No. 14/382,113, 371(c) date: Aug. 29, 2014.

Non-final Office Action dated Feb. 5, 2016, in U.S. Appl. No. 14/942,478, filed Nov. 16, 2015.

International Search Report for International Patent Application No. PCT/US2016/058290, U.S. Commissioner of Patents, United States, dated Jan. 24, 2017, 3 pages.

Written Opinion of the International Searching Authority for International Patent Application No. PCT/US2016/058290, U.S Commissioner of Patents, United States, dated Jan. 24, 2017, 9 pages.

Janeway, C.A., et al., "The Structure of a typical antibody molecule," Immunobiology: The Immune System in Health and Disease. $5^{th}$ edition. New York: Garland Science, United States (2001), Retrieved from https://www.ncbi.nlm.nih.gov/books/NBK27144/ on Dec. 13, 2016.

Rosler, E.S., et al., "An in vivo competitive repopulation assay for various sources of human hematopoietic stem cells," *Blood* 96(10): 3414-3421, The American Society of Hematology, United States (2000).

International Search Report for International Patent Application No. PCT/US2016/058300, U.S. Commissioner of Patents, United States, dated Feb. 28, 2017, 4 pages.

Written Opinion of the International Searching Authority for International Patent Application No. PCT/US2016/058300, U.S. Commissioner of Patents, United States, dated Feb. 28, 2017, 8 pages.

Extended European Search Report for European Patent Application No. 16858386.2, European Property Office, Munich, Germany, dated May 13, 2019, 7 pages.

Extended European Search Report for European Patent Application No. 16858381.3, European Patent Office, The Hague, Netherlands, dated Jun. 11, 2019, 13 pages.

Non-final Office Action dated Jul. 3, 2019, in U.S. Appl. No. 15/331,081, filed Oct. 21, 2016, 31 pages.

Lloyd, C., et al., "Modelling the Human Immune Response: Performance of a $10^{11}$ Human Antibody Repertoire Against a Broad Panel of Therapeutically Relevant Antigens," Protein Engineering, Design and Selection, 22(3):159-168, Oxford University Press, England (2009).

Brown, M., et al., "Tolerance to Single, but not Multiple, Amino Acid Replacements in Antibody $V_H$ CDR2: A Means of Minimizing B Cell Wastage from Somatic Hypermutation?," Journal of Immunology 156(9):3285-3291, American Association of Immunologists, United States (1996).

Vajdos, F.F., et al., "Comprehensive Functional Maps of the Antigen-Binding Site of an Anti-ErbB2 Antibody obtained with Shotgun Scanning Mutagenesis," Journal of Molecular Biology 320(2):415-428, Elsevier Science, United States (2002).

Harlow, E. and Lane, D., eds., "Antibodies: A Laboratory Manual," 3:23-24, 3:26, 4:37-47, 5:55-59, and 5:72-76, Cold Spring Harbor Laboratory, United States (1988).

\* cited by examiner

Level 0 Swab Sample (No Bed Bugs) Extracted in 350 μl Extraction Buffer 1.

Level 8 Swab Sample Extracted in 350 μl Extraction Buffer 2.

| Dilution of Swab Sample | | | | | | | | | |
|---|---|---|---|---|---|---|---|---|---|
| Buffer | 1/2048 | 1/1024 | 1/512 | 1/256 | 1/128 | 1/64 | 1/32 | 1/16 | 1/8 | 1/4 | 1/2 |

FIG. 11

Level 3 Swab Sample Extracted in 350 µl Extraction Buffer 3.

| | Dilution of Swab Sample | | | | | | | | |
|---|---|---|---|---|---|---|---|---|---|
| Buffer | 1/512 | 1/256 | 1/128 | 1/64 | 1/32 | 1/16 | 1/8 | 1/4 | 1/2 |

FIG. 13

Level 5 Swab Sample Extracted in 350 µl Extraction Buffer 3.

Level 7 Swab Sample Extracted in 350 µl Extraction Buffer 3.

| Buffer | Dilution of Swab Sample | | | | | | | | | | | |
|---|---|---|---|---|---|---|---|---|---|---|---|---|
| | 1/4096 | 1/2048 | 1/1024 | 1/512 | 1/256 | 1/128 | 1/64 | 1/32 | 1/16 | 1/8 | 1/4 | 1/2 |

FIG. 16

ANTI-BED BUG MONOCLONAL ANTIBODIES AND METHODS OF MAKING AND USES THEREOF

CROSS-REFERENCE TO RELATED APPLICATION

This application claims the benefit of the filing date of U.S. Appl. No. 62/244,189, filed Oct. 21, 2015, which is hereby incorporated by reference in its entirety.

FIELD

The present disclosure relates to anti-bed bug monoclonal antibodies, compositions comprising such antibodies, and methods of making and using such antibodies.

BACKGROUND

The scale and the number abed bug infestations in the United States have increased for over a decade. Bed bugs are commonly found in multi-unit housing, such as apartments, dormitories, nursing homes, and hotels, and public venues such as theaters, public transportation, and shopping malls.

While bed bugs are not known vectors of any pathogen, there is some evidence that bed bugs could act as mechanical vectors of Hepatitis B virus (Blow et al., *J. Med. Entomol.* 38: 694-700 (2001)). Methicillin-resistant *Staphylococcus aureus* (MRSA) and vancomycin-resistant *Enterococcus faecium* were recovered from bed bugs associated with a homeless shelter (Lowe et al., *Emerg. Infect. Dis.* 17: 1132-1134 (2011)).

Detection strategies currently in use include:
Visual detection: Personally checking mattresses and bedsprings, upholstery, and carpets for bed bugs, shed exoskeletons, or fecal droplets takes time and is often complicated by cryptic, inaccessible harborages;
Canine detection: Results with bed bug-sniffing dogs are highly variable. Success depends on the dog and trainer and type of entrainment and reward. Canine detection yields unacceptably high numbers of false positives, and its conspicuousness results in unpleasant public relations;
Active or passive monitors. Active monitors—such as Verdi® by FMC, CDC3000® by Stern Environmental, or NightWatch® by BioSensory, Inc. rely on custom pheromone blends or carbon dioxide, to attract bed bugs to a trap. Passive monitors, such as the ClimbUp® Insect interceptor, are placed near a sleeping person and use the heat and carbon dioxide of that person to attract and trap bed bugs. The efficacy of active and passive monitors depends on bed bug population density and may miss or underestimate small introductions of bugs. Most monitors also have an unacceptably large footprint, require specially trained personnel, and cost too much, in addition, both strategies involve actually handling dead bugs, which most people find unpleasant;
Other approaches to bed bug detection include:
Multiplex polymerase chain reaction (PCR) to distinguish bed bug eggs or bug fragments from human dwellings. This technique depends on physically recovering eggs or bug fragments and processing them using standard molecular biology reagents and techniques (Szalanski et al., *J. Med. Entomol.* 48: 937-940 (2011));
Microextraction of air samples to identify two well-characterized volatile pheromones, (E)-2-hexenal and (E)-2-oetenal, by gas chromatography and mass spectrometry (Eom et al., *Anal Chim Acta* 716: 2-10 (2012));
The use of infrared sensors, microphones, and a piezoelectric sensor to detect locomotion (Mankin et al., *J. Econ. Entomol.* 103: 1636-1646 (2010));
The detection of nitrophorin, a bed bug-specific salivary antigen (U.S. Pat. No. 7,743,552);
The detection of human blood antigens in bed bug excreta (U.S. Pat. No. 8,460,890): and
The detection of bed bug antigens by polyclonal antibodies (U.S. Publication No. 2015/0064727).

The number of available detection options is limited and there is a need for a convenient, easy-to-use detection method that rapidly, reproducibly, effectively, and directly detects bed hugs. In contrast to the prior approaches, the present invention provides monoclonal antibodies that satisfy the need.

SUMMARY

The present invention is directed to an antibody produced by the hybridoma deposited at the American Type Culture Collection (ATCC) under Accession Number PTA-122644 [BB2], or an antigen-binding fragment thereof.

The present invention is directed to an antibody produced by the hybridoma deposited at the ATCC under Accession Number PTA-112645 [BB7], or an antigen-binding fragment thereof.

The present invention is directed to a monoclonal antibody or an antigen-binding fragment thereof comprising the heavy chain and light chain complementarity determining regions (CDRs) of an antibody produced by the hybridoma deposited at the ATCC under Accession Number PTA-122644 [BB2] or an antibody produced by the hybridoma deposited at the ATCC under Accession Number PTA-122645 [BB7]. In certain embodiments, the antibody or antigen-binding fragment thereof comprises the heavy and light chain variable regions of the antibody produced by the hybridoma deposited at the ATCC under Accession Number PTA-122644 [BB2] or the antibody produced by the hybridoma deposited at the ATCC under Accession Number PTA-122645 [BB7]. In certain embodiments, the antibody or antigen-binding fragment thereof comprises the heavy and light chains of the antibody produced by the hybridoma deposited at the ATCC under Accession Number PTA-122644 [BB2] or the antibody produced by the hybridoma deposited at the ATCC under Accession Number PTA-122645 [BB7].

In certain embodiments, the antibody or antigen-binding fragment of any of the above inventions and embodiments is capable of binding to a bed bug antigen in a lysate of whole bed bugs or an extract of collection paper comprising bed hug waste material.

The present invention is directed to a mutant of an antibody produced by the hybridoma deposited at the ATCC under Accession Number PTA-122644 [BB2] or a mutant of an antibody produced by the bybridoma deposited at the ATCC under Accession Number PTA-122645 [BB7], wherein the mutant is capable of binding to a bed bug antigen in a lysate of whole bed bugs or an extract of collection paper comprising bed bug waste material.

The present invention is directed to a conjugated monoclonal antibody or a conjugated antigen binding fragment comprising any of the antibodies, antigen-binding fragments, or mutants of the above inventions or embodiments and a detection agent. In certain embodiments, the detection agent is colloidal gold. In certain embodiments, the conjugated antibody or conjugated antigen-binding fragment comprises an antibody produced by the hybridoma deposited at the ATCC under Accession Number PTA-122644 [BB2], or an antigen-binding fragment thereof, or an antibody produced by the hybridoma deposited at the ATCC under Accession Number PTA-122645 [BB7], or an antigen-binding fragment thereof.

The present invention is directed to a composition comprising any of the antibodies, antigen-binding fragments, mutants, or conjugated antibodies or conjugated antigen-binding fragments of the above inventions or embodiments, or a combination thereof. In certain embodiments, the composition comprises an antibody produced by the hybridoma deposited at the ATCC under Accession Number PTA-122644 [BB2] and an antibody produced by the hybridoma deposited at the ATCC under Accession Number PTA-122645 [BB7]. In certain embodiments, the composition comprises an antibody produced by the hybridoma deposited at the ATCC under Accession Number PTA-122644 [BB2], and a conjugated antibody comprising the antibody produced by the hybridoma deposited at the ATCC under Accession Number PTA-122645 [BB7] and a detection agent. In certain embodiments, the composition comprises an antibody produced by the hybridoma deposited at the ATCC under Accession Number PTA-122645 [BB7], and a conjugated antibody comprising the antibody produced by the hybridoma deposited at the ATCC under Accession Number PTA-122644 [BB2] and a detection agent.

The present invention is directed to a kit comprising any of the above inventions or embodiments, or a combination thereof.

The present invention is directed to a hybridoma capable of producing an antibody, wherein the hybridoma is deposited at the ATCC under Accession Number PTA 122644 [BB2] or wherein the hybridoma is deposited at the ATCC under Accession Number PTA-122645 [BB7].

The present invention is directed to an isolated cell producing an antibody, antigen-binding fragment, or mutant of any of the above inventions or embodiments.

The present invention is directed to a method of making an antibody, antigen-binding fragment, or mutant of any of the above inventions or embodiments, comprising culturing an isolated cell producing the antibody, antigen-binding fragment, or mutant, and isolating the antibody, antigen-binding fragment, or mutant from the cultured cell.

The present invention is directed to a method of detecting bed bugs, comprising contacting a sample comprising a bed bug antigen with any of the antibodies, antigen-binding fragments, mutants, conjugated antibodies or conjugated antigen-binding fragments, or compositions of the above inventions or embodiments, or a combination thereof, and detecting binding of the bed bug antigen to the antibody or antigen-binding fragment, mutant, conjugated antibody or conjugated antigen-binding fragment, composition, or combination thereof. In certain embodiments, the sample is contacted with an antibody of any of the above inventions or embodiments and a conjugated antibody of any of the above inventions or embodiments, in certain embodiments, the antibody is produced by the hybridoma deposited at the ATCC under Accession Number PTA-122644 [BB2], and the conjugated antibody comprises the antibody produced by the hybridoma deposited at the ATCC under Accession Number PTA-122645 [BB7] and a detection agent. In certain embodiments, the antibody is produced by the hybridoma deposited at the ATCC under Accession Number PTA-122645 [BB7], and the conjugated antibody comprises the antibody produced by the hybridoma deposited at the ATCC under Accession Number PTA-122644 [BB2] and a detection agent, in certain embodiments, the detecting comprises performing a lateral flow assay. In certain embodiments, the method further comprises collecting a sample comprising the bed bug antigen with a collection device and extracting antigens from the sample. In certain embodiments, the collection device is a swab.

BRIEF DESCRIPTION OF THE FIGURES

FIGS. 6-7 show noticeable dirt and residue for less dilute samples at the bottom of the test strips associated with the higher levels of bed bug infestation.

In FIG. 8A, the x-axis "concentration" is the dilution associated with the measured swab samples, and the y-axis is the value for the "test line area" provided by the Axxin test strip reader. In FIG. 8B, the value obtained for buffer 1 as a negative control (i.e., "Bo") was divided by itself to yield a normalized value of 1. The negative control reading (Bo) was then divided by the test line area 03) for each test sample dilution in the level, where smaller values under 1 suggest larger amounts of bed bug antigen and values above 1 indicate absence of bed bug antigen.

FIGS. 9-11 show the results of a lateral flow immunoassay for swab samples obtained from the noted levels of bed bug infestation. Swab samples were extracted in extraction buffer 2 containing 1× Tris-HCl (pH 7.6), 0.05% NaN$_3$, 0.1%

BSA, and 0.2% Tween-20 and the noted dilutions were applied to test strips. FIG. 11 shows noticeable dirt and residue for less dilute samples at the bottom of the test strips associated with the higher levels of bed bug infestation. Labeling of the strips and interpretation of results is as described for FIGS. 2-7.

FIGS. 13-17 show the results of a lateral flow immunoassay for swab samples obtained from the noted levels of bed bug infestation. Swab samples were extracted in extraction buffer 3 containing 1× Tris-HCl (pH 7.6), 0.05% NaN$_3$, 0.25% BSA, and 0.1% Tween-20 and the noted dilutions were applied to test strips. FIGS. 16-17 show noticeable dirt and residue for less dilute samples at the bottom of the test strips associated with the higher levels of bed bug infestation. Labeling of the strips and interpretation of results is as described for FIGS. 2-7.

DETAILED DESCRIPTION

Figure 1:
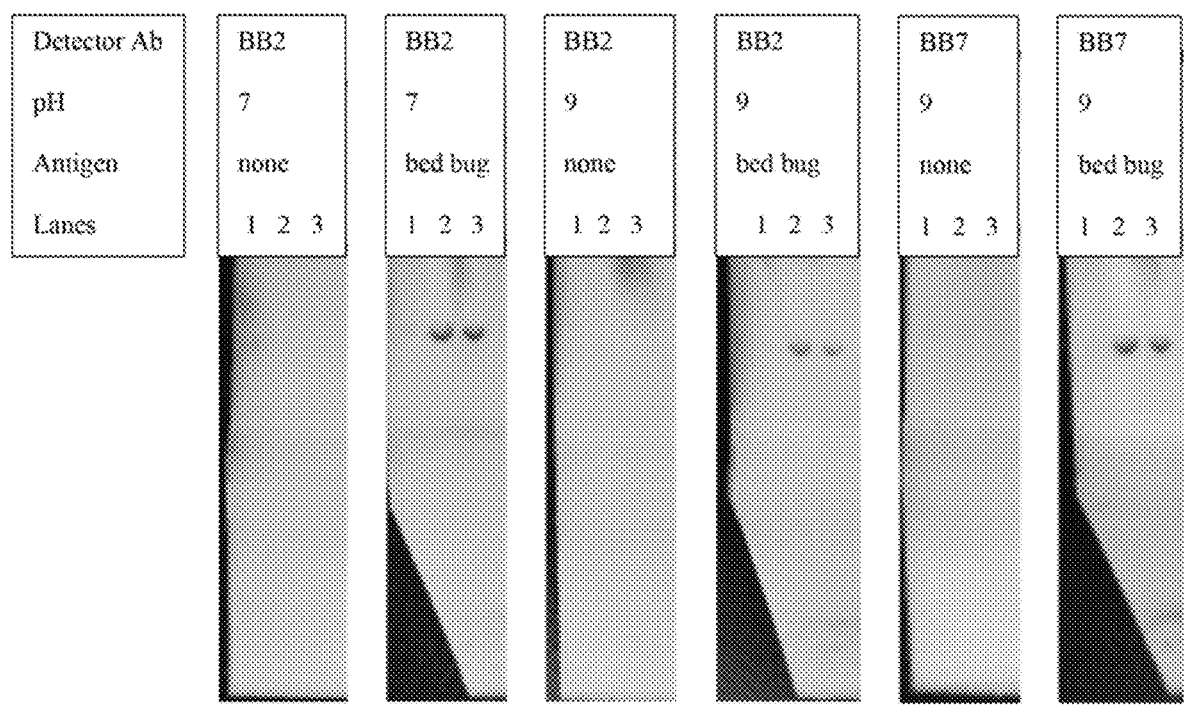
FIG. 1 shows the results of a sandwich capture assay using the BB2 and BB7 anti-bed bug monoclonal antibodies, Nitrocellulose strips are shown with binding of bed bug antigen indicated by dots associated with the presence of gold-conjugated BB2 or BB7 monoclonal antibody ("Detector Ab"), with the pH of the gold-conjugated antibody as indicated. Test strips are indicated by "bed bug" for the antigen. Negative control strips are indicated by "none" for the antigen, with PBS added to the strips instead of bed bug antigen. The capture antibodies associated with lanes 1-3 were rabbit polyclonal anti-bed bug antibody (lane 1), the BB2 monoclonal antibody (lane 2), and the BB7 monoclonal antibody (lane 3).

Provided herein are monoclonal antibodies and antigen-binding fragments thereof that hind to a bed hug antigen, compositions and kits comprising the antibodies and antigen-binding fragments, hybridomas, polypeptides, polynucleotides, vectors, cells capable of producing the antibodies and antigen-binding fragments, methods of making the antibodies and antigen-binding fragments, and methods of using the antibodies and antigen-binding fragments, for example, in the detection of bed bugs.

Terminology

As used herein, the term "bed bug" refers to any *Cimex* species or strain thereof.

The terms "antibody" and "antibodies" are terms of art and can be used interchangeably herein to refer to a molecule or molecules with an antigen-binding site that specifically binds an antigen.

The term "monoclonal antibody" refers to a homogeneous antibody population involved in the specific recognition and binding of a single antigenic determinant, or epitope. This is in contrast to polyclonal antibodies that typically include different antibodies directed against different antigenic determinants. Furthermore, "monoclonal antibody" refers to such antibodies made in any number of manners, including, but not limited to, by hybridoma, phage selection, recombinant expression, and transgenic animals.

The term "antigen-binding fragment" refers to a portion of an antibody that is capable of specifically binding to an antigen. Examples of antibody fragments include, but are not limited to heavy chain variable region fragments, light chain variable region fragments, Fab, Fab', F(ab')2, scFv fragments, Fv fragments, linear antibodies, single chain antibodies, multispecific antibodies, minibodies diabodies, triabodies, and tetrabodies.

The terms "variable region" or "variable domain" are terms of art and can be us d interchangeably herein to refer to a portion of an antibody that differs extensively in sequence among antibodies and is used in the binding and specificity of a particular antibody for its particular antigen. The variable regions of the heavy and light chain each consist of four framework regions (FR) connected by three complementarity determining regions (CDRs) also known as hypervatiable regions. The CDRs in each chain contribute to the formation of the antigen-binding site of antibodies.

The term "specifically binds" refers to molecules that bind to an antigen (e.g., epitope or immune complex) as such binding is understood by one skilled in the art. For example, a molecule that specifically binds to an antigen can bind to other peptides or polypeptides, generally with lower affinity as determined by, e.g., immunoassays, BIAcore®, KinExA 3000 instrument (Sapidyne Instruments, Boise, Id.), or other assays known in the art.

As used herein, the term "detecting" encompasses quantitative and qualitative detection.

As used herein, the term "effective amount" refers to the amount of that achieves a desired effect.

As used herein, the terms "host cell" and "cell" can be used interchangeably and can refer to any type of cell, e.g., a primary cell, a cell in culture, or a cell from a cell line, including a hybridoma.

An antibody, antigen-binding fragment, host cell, and cell as referred to herein includes "isolated" forms that have been separated or recovered from a component of their native environment, such as separation or removal from contaminants that would interfere with uses of the antibody, antigen-binding fragment, host cell, or cell, in which such contaminants may include enzymes, hormones, and other proteinaceous or nonproteinaceotis materials.

Monoclonal Antibodies, Compositions, Kits, Hybridomas, Polypeptides, Polynucleotides, Vectors, Cells, and Methods of Making The present invention is directed to an antibody produced by the hybridoma deposited at the American Type Culture Collection (ATCC) under Accession Number PTA-122644, or an antigen-binding fragment thereof. The anti-bed bug monoclonal antibody designated herein as BB2 is produced by the hybridoma deposited at the ATCC under Accession Number PTA-122644.

The present invention is directed to an antibody produced by the hybridoma deposited at the ATCC under Accession Number PTA-122645, or an antigen-binding fragment thereof. The anti-bed bug monoclonal antibody designated herein as BB7 is produced by the hybridoma deposited at the ATCC under Accession Number PTA-122645.

The present invention is directed to a monoclonal antibody or an antigen binding fragment thereof comprising the heavy chain and light chain complementarity determining regions (CDRs) of the antibody produced by the hybridoma deposited at the ATCC under Accession Number PTA-122644 [BB2] or the antibody produced by the hybridoma deposited at the ATCC under Accession Number PTA-122645 [BB7] (see e.g., the discussion of CDRs in Kabat et al., U.S. Dept. of Health and Human Services, "Sequences of Proteins of Immunological Interest" (1983), and Chothia et al., *J. Mol. Biol.* 196:901-917 (1987)). Methods for determining CDRs are well-known, including an approach based on cross-species sequence variability (i.e., Kabat et al.

Sequences of Proteins of Immunological Interest, (5th ed., 1991, National Institutes of Health, Bethesda, Md.)), and an approach based on crystallographic studies of antigen-antibody complexes (Al-lazikani et al., *J. Molec. Biol.* 273:927-948 (1997)). In addition, combinations of these two approaches can be used to determine CDRs. CDRs also can be determined according to Lefranc M-P, *The Immunologist* 7: 132-136 (1999); Lefranc M-P, et al., *Nucleic Acid Res* 27: 209-212 (1999); MacCallum R M et al., *J. Mol. Biol.* 262: 732-745 (1996); Martin A. "Protein Sequence and Structure Analysis of Antibody Variable Domains," in *Antibody Engineering*, Kontemiann and Dübel, eds., Chapter 31, pp. 422-439, Springer-Verlag, Berlin (2001); and Oxford Molecular's AbM antibody modeling software (Oxford Molecular Group, Inc.).

In certain embodiments, the antibody or antigen-binding fragment thereof comprises the heavy and light chain variable regions of the antibody produced by the hybridoma deposited at the ATCC under Accession Number PTA-122644 [BB2] or the antibody produced by the hybridoma deposited at the ATCC under Accession Number PTA-122645 [BB7]. Generally, a variable region is located at about the amino-terminal 110 to 120 amino acids in the mature heavy chain and about the amino-terminal 90 to 115 amino acids in the mature light chain.

In certain embodiments, the antibody or antigen-binding fragment thereof comprises the hear and light chains of the antibody produced by the hybridoma deposited at the ATCC under Accession Number PTA-122644 [BB2] or the antibody produced by the hybridoma deposited at the ATCC under Accession Number PTA-122645 [BB7]. Each heavy chain comprises a heavy chain variable region and a heavy chain constant region. The heavy chain constant region comprises three domains, CH1, CH2 and CH3. Each light chain comprises a light chain variable region and a light chain constant region. The light chain constant region comprises one domain (CL1).

The monoclonal antibodies of the invention can include, but are not limited to, recombinantly produced antibodies, human antibodies, humanized antibodies, chimeric antibodies, multispecific antibodies such as bispecific antibodies, fusion proteins comprising an antigen determination portion of an antibody, and any other modified immunoglobulin molecule comprising an antigen recognition site so long as the antibodies exhibit the desired activity. Antibodies can be of any type (e.g., IgG, IgE, IgM, IgD, IgA, or IgY), any class (e.g., $IgG_1$, $IgG_2$, $IgG_3$, $IgG_4$, $IgA_1$, or $IgA_2$), or any subclass (e.g., $IgG_{2a}$ or $IgG_{2b}$) of immunoglobulin molecule. Techniques for the production of antibodies will be apparent to the skilled practitioner.

Monoclonal antibodies can be prepared, for example, using hybridoma methods, such as those described by Kohler and Milstein, *Nature* 256:495 (1975). Using the h hybridoma method, a mouse, hamster, or other appropriate host animal, is immunized to elicit the production by lymphocytes of antibodies that will specifically bind to an immunizing antigen. Lymphocytes can also be immunized in vitro. Following immunization, the lymphocytes are isolated and fused with a suitable myeloma cell line using, for example, polyethylene glycol, to form hybridoma cells that can then be selected away from unfused lymphocytes and myeloma cells.

Monoclonal antibodies can also be made using recombinant DNA methods as described in U.S. Pat. No. 4,816,567. The polynucleotides encoding a monoclonal antibody are isolated from mature B-cells or hybridoma cell, such as by RT-PCR using oligonucleotide primers that specifically amplify the genes encoding the heavy and light chains of the antibody, and their sequence is determined using conventional procedures. The isolated polynucleotides encoding the heavy and light chains are then cloned into suitable expression vectors, which allow for generation of monoclonal antibodies when transfected into host cells, including, but not limited to, *E. coli* cells, simian COS cells, Chinese hamster ovary (CHO) cells, or myeloma cells. Also, recombinant monoclonal antibodies or fragments thereof of the desired species can be isolated from phage display libraries expressing CDRs of the desired species (see, e.g., McCafferty et al., *Nature* 348:552-554 (1990); Clackson et al., *Nature* 352:624-628 (1991); and Marks et al., *J. Mol. Biol.* 222:581-597 (1991)).

Antigen-binding fragments of the invention can be produced by any known method and include a portion of an antibody that is capable of specifically binding to an antigen. Examples of antibody fragments include, but are not limited to, heavy chain variable region fragments, light chain variable region fragments, Fab, Fab', F(ab')2, scFv fragments, Fv fragments, linear antibodies, single chain antibodies, multispecific antibodies, minibodies, diabodies, triabodies, and tetrabodies see, e.g., Hudson and Souriau, *Nature Med.* 9: 129-134 (2003) and U.S. Pat. No. 5,641,870). Traditionally, these fragments are derived via proteolytic digestion of intact antibodies (see, e.g., Morimoto et al., *Journal of Biochemical and Biophysical Methods* 24:107-117 (1993); Brennan et al., *Science* 229:81 (1985)). In certain embodiments, antibody fragments are produced recombinantly. For example, antibody fragments can be expressed in and secreted from *E. coli* or other host cells, thus allowing the production of large amounts of the fragments. Such antibody fragments can also be isolated from the antibody phage libraries. Other techniques for the production of antibody fragments will be apparent to the skilled practitioner.

In certain embodiments, any of the above-mentioned antibodies or antigen-binding fragments thereof is capable of binding to a bed bug antigen in a lysate of whole bed bugs or an extract of collection paper comprising bed bug waste material. The methods for producing lysates of whole bed bugs and extracts of collection paper comprising bed bug waste material will be apparent to the skilled practitioner based on known extraction techniques and the methods disclosed in Example 1. Whole bed bugs include nymphs, males, and/or females can be obtained from an area of infestation or an experimentally or commercially maintained bed bug colony, and can include any *Cimex* species or strain, including, but not limited to, *Cimex lectularius* and the Harlan strain. Collection paper comprising bed bug waste material can include bed bug excreta and/or tissues, for example, and can be obtained from commercial sources as discussed in Example 1.

The present invention is also directed to a mutant of the antibody produced by the hybridoma deposited at the ATCC under Accession Number PTA-122644 [BB2] or the antibody produced by the hybridoma deposited at the ATCC under Accession Number PTA-122645 [BB7]. Mutants can contain, for example, conservative substitution mutations, i.e. the substitution of one or more amino acids by similar amino acids. For example, conservative substitution refers to the substitution of an amino acid with another within the same general class such as, for example, one acidic amino acid with another acidic amino acid, one basic amino acid with another basic amino acid or one neutral amino acid by another neutral amino acid. What is intended by a conservative amino acid substitution is well known in the art. Mutations can also include deletions, insertions, inversions, and repeats. Mutations can be introduced by general molecular biology methods known in the art including, but not limited to, error-prone PCR, oligonucleotide-directed mutagenesis, site-directed mutagenesis, and heavy or light chain shuffling.

The present invention is directed to a monoclonal antibody or antigen-binding fragment thereof having one or more characteristics that are substantially similar to those of the antibody produced by the hybridoma deposited at the ATCC under Accession Number PTA-122644 [BB2] or the antibody produced by the hybridoma deposited at the ATCC under Accession Number PTA-122645 [BB7]. The phrase "substantially similar" as used herein denotes a sufficiently high degree of similarity between two characteristics such that one of skill in the art would consider the difference to be of little or no biological and/or statistical significance. In certain embodiments, the difference between two numerical values can be less than about 15%, 10%, 5%, 2%, or 1%. The characteristics of the deposited antibodies can include one or more properties, such as, but not limited to, binding specificity (e.g., Kd value), antigenic determinants/epitope, and polynucleotide or polypeptide sequences. In certain embodiments, the monoclonal antibody or antigen-binding fragment thereof has a polynucleotide or polypeptide sequence that is at least 90%-99%, at least 95%-99%, at least 90%, at least 95%, at least 96%, at least 97%, at least 98%, or at least 99% identical to the polynucleotide or polypeptide sequence of the antibody produced by the hybridoma deposited at the ATCC under Accession Number PTA-122644 [BB2] or the antibody produced by the hybridoma deposited at the ATCC under Accession Number PTA-122645 [BB7]. In certain embodiments, the monoclonal antibody or antigen-binding fragment thereof has one or more of the same characteristics as the antibody produced by the hybridoma deposited at the ATCC under Accession Number PTA-122644 [BB2] or the antibody produced by the hybridoma deposited at the ATCC under Accession Number PTA-122645 [BB7]. In certain embodiments, the monoclonal antibody or antigen-binding fragment thereof binds to the same antigenic determinant/epitope as the antibody produced by the hybridoma deposited at the ATCC under Accession Number PTA-122644 [BB2] or the antibody produced by the hybridoma deposited at the ATCC under Accession Number PTA-122645 [BB7].

The term "epitope" or "antigenic determinant" can be used interchangeably herein to refer to that portion of an antigen capable of being recognized and specifically bound by a particular antibody. An epitope typically includes at least 3, and more usually, at least 5 or 8-10 amino acids in a unique spatial conformation. An epitope can be, for example, contiguous amino acids of a polypeptide (linear or contiguous epitope) or an epitope can, for example, come together from two or more non-contiguous regions of a polypeptide or polypeptides (conformational, non-linear, discontinuous, or non-contiguous epitope). The epitope to which an antibody binds can be determined by, e.g., NMR spectroscopy, X-ray diffraction crystallography studies, ELISA assays, hydrogen/deuterium exchange coupled with mass spectrometry (e.g., liquid chromatography electrospray mass spectrometry), array-based oligo-peptide scanning assays, and/or mutagenesis mapping (e.g., site-directed mutagenesis mapping). For X-ray crystallography, crystallization may be accomplished using any of the known methods in the art (e.g., Giegé R et al., (1994) Acta Crystallogr D Biol Crystallogr 50(Pt 4): 339-350; McPherson A (1990) Eur J Biochem 189: 1-23; Chayen N E (1997) Structure 5: 1269-1274; McPherson A (1976) J Biol Chem 251: 6300-6303). Antibody:antigen crystals can be studied using well known X-ray diffraction techniques and can be refined using computer software such as X-PLOR (Yale University, 1992, distributed by Molecular Simulations, Inc.; see, e.g., Meth Enzymol (1985) volumes 114 & 115, eds Wyckoff H W et al.; U.S. 2004/0014194), and BUSTER (Bricogne G (1993) Acta Crystallogr D Biol Crystallogr 49(Pt 1): 37-60; Bricogne G (1997) Meth Enzymol 276A: 361-423, ed Carter C W; Roversi P et al., (2000) Acta Crystallogr D Biol Crystallogr 56(Pt 10): 1316-1323), Mutagenesis mapping studies can be accomplished using any method known to one of skill in the art. See, e.g., Champe M et al., (1995) J Biol Chem 270; 1388-1394 and Cunningham B C & Wells J A (1989) Science 244: 1081-1085 for a description of mutagenesis techniques, including alanine scanning mutagenesis techniques.

The present invention is directed to a conjugated monoclonal antibody or conjugated antigen-binding fragment comprising any of the antibodies, antigen binding fragments, or mutants of the invention and a detection agent. The detection agent can be conjugated directly or indirectly to the antibody, antigen-binding fragment, or mutant. The detection agent can be detectable by itself or, in the case of an enzymatic label, can catalyze chemical alteration of a substrate compound or composition which is detectable. The detection agent includes, but is not limited to, a radiolabel, a fluorophore, a chromophore, an imaging agent, or a metal, including a metal ion. In certain embodiments, the detection agent is colloidal gold or gold nanoparticles. In certain embodiments, the colloidal gold or gold nanoparticles is comprised of gold particles having a size of 1-300 nm, 1-250 nm, 10-200 nm, 20-150 nm, 20-100 nm, 20-80 nm, 20-60 nm 20-50 nm, 20 nm, 30 nm, 40 nm, 50 nm, 60 nm, 70 nm, 80 nm, 90 nm, 100 nm, 150 nm, 200 nm, 250 nm, or 300 nm. In certain embodiments, the conjugated antibody or conjugated antigen-binding fragment comprises the antibody produced by the hybridoma deposited at the ATCC under Accession Number PTA-122641 [BB2], or an antigen-binding fragment thereof, or the antibody produced by the hybridoma deposited at the ATCC under Accession Number PTA-122645 [BB7], or an antigen-binding fragment thereof.

The present invention is directed to a composition comprising any of the antibodies or antigen binding fragments thereof, mutants, or conjugated antibodies or conjugated antigen-binding fragments of the invention, or a combination thereof. In certain embodiments, the composition comprises the antibody produced by the hybridoma deposited at the ATCC under Accession Number PTA-122644 [BB2] and the antibody produced by the hybridoma deposited at the ATCC under Accession Number PTA-122645 [BB7]. In certain embodiments, the composition comprises the antibody produced by the hybridoma deposited at the ATCC under Accession Number PTA-122644 [BB2], and a conjugated antibody comprising the antibody produced by the hybridoma deposited at the ATCC under Accession Number PTA-122645 [BB7] and a detection agent. In certain embodiments, the composition comprises the antibody produced by the hybridoma deposited at the ATCC under Accession Number PTA-122645 [BB7], and a conjugated antibody comprising the antibody produced by the hybridoma deposited at the ATCC under Accession Number PTA-122644 [BB2] and a detection agent.

The present invention is directed to a kit comprising any of the antibodies or antigen binding fragments thereof, mutants, conjugated antibodies or conjugated antigen-binding fragments, or compositions of the invention, or a combination thereof. In certain embodiments, a kit comprises at least one component in one or more containers. In some embodiments, the kit comprises components necessary and/or sufficient to perform a detection assay, including controls, directions for performing assays, any necessary device, and/or software for analysis and presentation of results. Suitable devices include those disclosed in U.S. Application No. 62/244,188 filed Oct. 21, 2015, titled "Bed Bugs Detection Device," and the U.S. non-provisional application and international PCT application thereof filed Oct. 21, 2016, which are incorporated by reference herein in their entireties, as well as U.S. Pat. Nos. 7,220,597 and 7,214,542, both of which are incorporated by reference herein in their entireties.

The present invention is directed to a hybridoma capable of producing an antibody, wherein the hybridoma is deposited at the ATCC under Accession Number PTA-122644 [BB2] or wherein the hybridoma is deposited at the ATCC under Accession Number PTA-122645 [BB7].

The present invention is directed to an isolated polypeptide comprising an amino acid sequence at least 90%-99%, at least 95%-99%, at least 90%, at least 95%, at least 96%, at least 97%, at least 98% or at least 99% identical to an amino acid sequence of a heavy or light chain variable region, or a heavy or light chain, of the antibody produced by the hybridoma deposited at the ATCC under Accession Number PTA-122644 [BB2] or the antibody produced by the hybridoma deposited at the ATCC under Accession Number PTA-122645 [BB7]. In certain embodiments, the polypeptide comprises the amino acid sequences of the CDRs of a heavy or light chain variable region of the antibody produced by the hybridoma deposited at the ATCC under Accession Number PTA-122644 [BB2] or the antibody produced by the hybridoma deposited at the ATCC under Accession Number PTA-122645 [BB7]. In certain embodiments, the polypeptide comprises the amino acid sequences of the heavy or light chain variable region, or heavy or light chain, of the antibody produced by the hybridoma deposited at the ATCC under Accession Number PTA-122644 [BB2] or the antibody produced by the hybridoma deposited at the ATCC under Accession Number PTA-122645 [BB7].

The present invention is directed to an isolated polynucleotide comprising a nucleic acid sequence at least 90%-99%, at least 95%-99%, at least 90%, at least 95%, at least 96%, at least 97%, at least 98% or at least 99% identical to a nucleic acid sequence encoding a heavy or light chain variable region, or a heavy or light chain, of the antibody produced by the hybridoma deposited at the ATCC under Accession Number PTA-122644 [BB2] or the antibody produced by the hybridoma deposited at the ATCC under Accession Number PTA-122645 [BB7]. In certain embodiments, the polynucleotide comprises nucleic acid sequences encoding the CDRs of a heavy or light chain variable region of the antibody produced by the hybridoma deposited at the ATCC under Accession Number PTA-122644 [BB2] or the antibody produced by the hybridoma deposited at the ATCC under Accession Number PTA-122645 [BB7]. In certain embodiments, the polynucleotide comprises a nucleic acid sequence encoding the heavy or light chain variable region, or heavy or light chain, of the antibody produced by the hybridoma deposited at the ATCC under Accession Number PTA-122644 [BB2] or the antibody produced by the hybridoma deposited at the ATCC under Accession Number PTA-122645 [BB7].

The present invention is directed to a vector comprising one or more of the isolated polynucleotides of the invention. In certain embodiments, the vector is an expression vector.

The present invention is directed to an isolated cell producing an antibody, antigen-binding fragment, or mutant of the invention. In certain embodiments, the cell is a hybridoma. In certain embodiments, the cell comprises one or more vectors of the invention. In certain embodiments, the cell comprises one or more polynucleotides of the invention.

The present invention is directed to a method of making an antibody, antigen-binding fragment, or mutant of the invention, comprising culturing an isolated cell producing the antibody, antigen-binding fragment, or mutant, and isolating the antibody, antigen-binding fragment, or mutant from the cultured cell.

Cells include, but are not limited to, hybridomas, prokaryotes, yeast, insect, or higher eukaryotic cells. Hybridomas that produce monoclonal antibodies can be propagated either in vitro culture using standard methods (coding, Monoclonal Antibodies: Principles and Practice, Academic Press, 1986) or in vivo as ascites tumors in an animal. Prokaryotes include gram negative or gram positive organisms, for example *E. coli* or bacilli. Higher eukaryotic cells include, but are not limited to, established cell lines of mammalian origin. Examples of suitable mammalian cell lines include COS-7, L, C127, 3T3, Chinese hamster ovary (CHO), HeLa, and BHK cell lines. In certain embodiments, any of the antibodies, antigen-binding fragments, or mutants of the invention are produced by isolated cells following transfection of the cells with vectors comprising polynucleotides encoding the sequences of the antibodies, antigen-binding fragments, or mutants of the invention. Appropriate cloning and expression vectors for use with bacterial, fungal, yeast, and mammalian cellular hosts are described by Pouwels et al. (Cloning Vectors: A Laboratory Manual, Elsevier, N.Y., 1985). Mammalian expression vectors can comprise nontranscribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a polyadenylation site, splice donor and acceptor sites, and transcriptional termination sequences. Baculovirus systems for production of heterologous proteins in insect cells are reviewed by and Luckow and Summers, Bio/Technology 6:47 (1988).

The antibodies, antigen-binding fragments, or mutants of the invention can be isolated front the cells or culture medium, or from ascites fluid for in vivo propagation of hybridomas. Isolation of the antibodies, antigen-binding fragments, or mutants can be according to any suitable method. Such standard methods include chromatography (e.g., ion exchange, affinity and sizing column chromatography), centrifugation, differential solubility, or by any other standard technique for protein purification. Methods known in the art for purifying antibodies and other proteins include, for example, those described in U.S. Patent Publication Nos. 2008/0312425, 2008/0177048, and 2009/0187005.

Methods of Detecting Bed Bugs

The present invention is directed to a method of detecting bed bugs, comprising contacting a sample comprising a bed bug antigen with any of the antibodies, antigen-binding fragments, mutants, conjugated antibodies or conjugated antigen-binding fragments, or compositions of the invention, or a combination thereof, and detecting binding of the bed bug antigen to the antibody or antigen-binding fragment, mutant, conjugated antibody or conjugated antigen-binding fragment, composition, or combination thereof. "A sample" includes, but is not limited to, whole bed bugs, bed bugs parts, bed bug waste material, lysates or extracts thereof, extracts of collection paper comprising bed bug waste material, and fluids containing the same.

The contacting can be by any suitable method. In certain embodiments, the contacting is by application of a sample comprising the bed bug antigen to an antibody, antigen-binding fragment, mutant, conjugated antibody or conjugated antigen-binding fragment, or composition of the invention, or a combination thereof that is immobilized or otherwise located on a surface. Any acceptable surface can be used, as will be appreciated by the skilled practitioner, including, but not limited to, a nitrocellulose membrane or a pad composed of a suitable material, and can include a sandwich, well, or lateral flow design. In certain embodiments, the sample is contacted with an antibody of the invention and a conjugated antibody of the invention. In certain embodiments, the antibody is produced by the hybridoma deposited at the ATCC under Accession Number PTA-122644 [BB2], and the conjugated antibody comprises the antibody produced by the hybridoma deposited at the ATCC under Accession Number PTA-122645 [BB7] and a detection agent. In certain embodiments, the antibody is produced by the hybridoma deposited at the ATCC under Accession Number PTA-122645 [BB7], and the conjugated antibody comprises the antibody produced by the hybridoma deposited at the ATCC under Accession Number PTA-112644 [BB2] and a detection agent. In certain embodiments, the contacting further comprises contacting the antibody, antigen-binding fragment, mutant, conjugated antibody or conjugated antigen-binding fragment, or composition of the invention, or a combination thereof with a control sample for comparison with the test sample.

The detecting can be by any suitable method and can include quantitative or qualitative detection. Such methods include, but are not limited to, antigen-binding assays that are well known in the art, such as lateral flow assays, radioimmunoassays, ELISA (enzyme linked immunosorbent assay), "sandwich" immunoassays, immunoprecipitation assays, fluorescent immunoassays, protein A immunoassays, and immunohistochemistry (IHC). The detection can include visual analysis of a colorimetric, fluorescent, or luminescent reaction, for example, or can include use of a device that measures such reactions. Suitable devices include those disclosed in U.S. Application No. 62/244,188 filed Oct. 21, 2015, titled "Bed Bugs Detection Device," and the U.S. non-provisional application and international PCT application thereof filed Oct. 21, 2016, which are incorporated by reference herein in their entireties, as well as U.S. Pat. Nos. 7,220,597 and 7,214,542, both of which are incorporated by reference herein in their entireties. In certain embodiments, the detecting comprises performing a lateral flow assay. In certain embodiments, the detecting occurs in 1-20 minutes, 1-15 minutes, 1-10 minutes, 1-5 minutes, 20 minutes or less, 15 minutes or less, 10 minutes or less, 5 minutes or less, within 20 minutes, within 15 minutes, within 10 minutes, or within 5 minutes.

The amount of the antibody, antigen-binding fragment, mutant, conjugated antibody or antigen-binding fragment, composition of the invention, or a combination thereof can include any effective amount, which will be apparent to a skilled practitioner based on known detection methods and the methods disclosed in the examples. The sample can be diluted or undiluted.

In certain embodiments, the method further comprises collecting a sample comprising the bed bug antigen with a collection device and extracting antigens from the sample. The sample can be collected from any surface associated with bed bug infestation, including, but not limited to, bedding, mattresses, upholstery, carpets, rugs, and furniture. The collection device can be any suitable device, including but not limited to a swab, such as a cotton swab, a vacuum, or any material that can be used to collect residue including, but not limited to, a wipe, tissue, or towelette. In certain embodiments the collection device is a swab. In certain embodiments, extracting antigens from the sample comprises solubilizing antigens in the sample with an extraction buffer. Suitable extraction buffers will be apparent to the skilled practitioner in view of well-known extraction buffers and those disclosed in the examples.

EXAMPLES

The examples in dais section are offered by way of illustration, and not by way limitation.

Example 1: Generation of Anti-Bed Bug Monoclonal Antibodies

Mice were immunized with whole bed bug lysates and bed bug paper extracts (i.e., extracts from bed bug collection paper containing waste material from a bed bug colony).

Whole bed butt lysates were produced from nymphs, males, and females from a bed bug colony (Harlan strain, i2LResearch USA Inc., Baltimore, Md., USA) that were frozen and triturated in IX phosphate buffered saline (PBS). The lysates were clarified by 0.45 micron syringe filter. Protein concentration was determined by a standard Bradford protein assay. The clarified, quantified extracts were aliquoted into 1.5 mL Eppendorf tubes and stored at −80° C.

Bed bug collection paper (i2LResearch USA Inc., Baltimore, Md., USA) was cut into approximately 1 $cm^2$ pieces and placed into 2 mL plastic centrifuge tubes. Extraction was performed by adding 1.0 mL of 50 mM PBS (pH 7.4) and mixing the tubes for 30 minutes on a tube rocker. After 30 minutes, the extract was fully extracted by passing the mixture through a 5 mL syringe. This collected extract was then used to obtain more extract from fresh collection paper by serially adding the extract to the newly cut paper and repeating the process. The final extract was then centrifuged at 12,000 rpm for 10 minutes to remove particulates. The supernatant was removed and retained, and the pelleted material was discarded. The protein concentration of the supernatant was determined by Bradford assay to be 0.6 mg/mL. The final solution (i.e., "bed bug paper extract") was stored at −20° C.

Four 4-5 week old Barbie mice (Harlan Laboratories, Inc., Indianapolis, Ind., USA) were immunized subcutaneously in the back with 50 μg whole bed bug lysate mixed with 100 μl of adjuvant. The adjuvant used for two of the mice was a traditional adjuvant (Freund's Adjuvant, Sigma-Aldrich Co. LLC, St. Louis, Mo., USA) and the adjuvant used for the remaining two mice was a water-soluble adjuvant (ImmuQuik®, KCH Scientific, San Jose, Calif., USA).

At Day 14 after the initial immunization, the immunized mice were boosted with 50 μg whole bed bug lysate mixed with 100 μl of an adjuvant as originally used for each mouse. At Day 37, sera from the mice were titer-tested using a standard enzyme immunoassay, using goat anti-mouse horseradish peroxidase conjugated antibody as the secondary antibody/enzyme conjugate and 3,3',5,5'-Tetramethylbenzidine as the chromogenic substrate, and 10 μg/ml whole bed bug lysate as the source of antigen. The two mice immunized with whole bed bug lysate in the water-soluble adjuvant produced higher titers. However, since the titers were not strong overall, all four immunized mice were boosted with double the amount of Whole bed bug lysate (i.e., 100 µg) at Day 51 and then again at Day 78. At Day 107, the four mice were boosted with 15 µl of bed bug paper extract. At Day 117, the mouse with the highest previous titer was titer-tested using whole bed bug lysate or bed bug paper extract as the source of antigen. A weak reaction was observed for bed bug paper extract. At Day 134, all four mice were boosted with 100 µl of bed bug paper extract using ImmuQuik® as the adjuvant. At Day 151, the mice were titer tested using bed bug paper extract as the source of antigen, and the highest titer mouse was boosted with 100 µl bed bug paper extract.

Spleen cells were collected from the two highest titer mice, one at Day 154 and the other at Day 216, and fused with murine SP 2/0 myeloma cells by using polyethylene glycol. The fused cells were cultured in selection medium for 10 days, followed by screening with bed bug paper extract as the source of antigen. About 41 positive clones were identified from primary screening, and about 25 positive clones were confirmed in secondary screening. Stable cell lines were subcloned, ascites were produced for more than 25 clones, and antibodies were purified (e.g., in amounts of 2-5 mg). Two antibodies referred to herein as the BB2 and BB7 antibodies were determined by enzyme immunoassay to have a strong reaction with bed bug paper extract as compared to antibodies from other clones and were selected for further study. Hybridomas producing the BB2 and BB7 antibodies were deposited under the Budapest Treaty at the American Type Culture Collection, Patent Depository, 10801 University Boulevard, Manassas, Va. 20110-2209, on Oct. 8, 2015, and given ATCC Accession No. PTA-122644 and ATCC Accession. No. PTA-122645, respectively.

Example 2: Sandwich Capture Assay of Anti-Bed Bug Monoclonal Antibodies

A sandwich capture assay was performed using the BB2 or BB7 antibody as a capture antibody and either gold-conjugated BB2 or gold-conjugated BB7 as a detector antibody. Bed bug paper extract as described in Example 1 was used as the source of bed bug antigen. A rabbit polyclonal anti-bed bug antibody as described in U.S. Publication No. 2015-0064727 was used as a positive control capture antibody and PBS was used as a negative control for the antigen.

Capture antibodies at concentrations of 2.0 mg/ml were spotted as 0.3 µl dots onto nitrocellulose paper strips. Bed bug paper extract was added to test strips and PBS was added to negative control strips. Gold-conjugated BB2 antibody (at pH 7 or 9) or gold conjugated BB7 antibody (at pH 9) was added as the detector antibody to the strips as shown in FIG. 1. The negative control strips showed an absence of binding by detector antibodies. Test strips showed red staining of the capture dots that indicated binding of the gold-conjugated detector antibodies to bed bug antigen immobilized on the nitrocellulose by the capture antibodies. As summarized in Table 1, strong reactions were observed with use of either the BB2 or BB7 antibody as the capture antibody. In contrast, very weak (i.e., "+") or uncertain (i.e., "+/−") reactions were observed with use of the rabbit polyclonal anti-bed bug antibody as the capture antibody.

TABLE 1

Observed Intensities in Sandwich Capture Assay

| Gold-conjugated detector antibody (pH) | Capture antibody | | |
|---|---|---|---|
| | Rabbit polyclonal anti-bed bug antibody | BB2 | BB7 |
| BB2 (7) | + | ++++ | +++ |
| BB2 (9) | + | +++ | ++ |
| BB7 (9) | +/− | ++++ | +++ |

Example 3: Lateral Flow Immunoassay to Detect Bed Bug Antigens

An example lateral flow immunoassay was designed to detect bed bug antigens from samples taken by swabbing areas of differing levels of bed bug Infestation, Extraction buffers were prepared and tested for efficient extraction of bed bug antigen from swabs, proper flow on nitrocellulose test strips, and low to no non-specific binding. Swab samples were extracted and serially diluted to investigate the sensitivity of the assay. Precision of the assay was investigated by testing replicates and reading signal intensities using a test strip reader.

Nitrocellulose Membrane Preparation:

Nitrocellulose membranes (CN 140, 25 mm, Sartorius Corp., Bohemia, N.Y., USA) were sprayed with 1.0 mg/mL of the BB7 anti-bed bug antibody as the test line and 0.5 mg/mL of goat anti-mouse antibody (Lampire Biological Laboratories, Pipersville, Pa., USA) as the control line using a Biodot Air Jet (Biodot. Irvine, Calif., USA) for striping the nitrocellulose membranes. Striping Buffer was 1×PBS, 0.2% Sucrose, pH 7.4. The test line and control line were sprayed 7 mm apart, with the test line located 10 mm from the bottom of the membrane. Membranes were striped at a rate of 1.0 µl/cm. The membranes were dried at 37° C. for 1 hour and stored in a desiccated foil pouch. Striped membranes were kept desiccated overnight before blocking.

Nitrocellulose Membrane Blocking:

After drying overnight, striped membranes were placed into a blocking solution (25 mM $KPO_4$, 0.2% Casein, 0.5% Boric Acid, 0.02% Sucrose, 0.1% Surfactant 10G, 0.5% PVA) with the orientation of the test line at the bottom of the nitrocellulose and the control line on the top of the nitrocellulose. The blocking solution was allowed to wick to the top of the membrane. The membranes were removed from the blocking solution and placed in a finger rack to dry at 37° C. for 1 hour. Blocked membranes were kept desiccated in a plastic bag and stored in a dry room.

Antibody Gold Conjugation:

A Slide-A-Lyzer™ disalysis cassette (10000 molecular weight cutoff, Thermo Fisher Scientific Inc., Carlsbad, Calif., USA) was used to dialyze the BB2 anti-bed bug antibody overnight in 10 mM $KPO_4$, pH 7.4. The final concentration of the BB2 antibody after dialyzing was 0.875 mg/ml. A colloidal gold solution containing 40 nm particles and an optical density (OD) of 2:28 at 525 nm was adjusted at room temperature to pH 8.6 with freshly made 0.1 M $K_2CO_3$. The dialyzed BB2 antibody was added to the colloidal gold solution while vortexing. The solution was incubated for 30 minutes on a rotator at room temperature.

The conjugate was blocked with 10 μl (for every 1 ml of OD 2 colloidal gold) of gold conjugate blocking buffer (25 mM KP04, 0.2% Bioterge, 6% BSA, 0.3% Sucrose) on a rotator at room temperature for 10 minutes. The gold conjugate was centrifuged at 12000 RPM 4° C. for 20 minutes and the supernatant was discarded. The conjugate pellet was re-suspended with 0.2 ml (for every 1 ml of OD 2 colloidal gold) re-suspension buffer (1:5 dilution of gold conjugate blocking buffer in 25 mM $KPO_4$, 0.05% Sodium Azide). The OD of the gold conjugated BB2 antibody was checked using a spectrophotometer and adjusted to 10. The gold conjugated BB2 antibody was stored at 4° C.

Gold Conjugate Pad Preparation:

A P-1000 pipette was used to saturate 300 mm Ahlstrom 8950 glass fiber conjugate pads (Ahlstrom, Helsinki, Finland) with blocking buffer (25 mM $KPO_4$, 0.2% Casein, 0.5% Boric Acid, 0.02% Sucrose, 0.1% Surfactant 10G, 0.5% PVA). After 15 minutes, the saturated conjugate pads were transferred to a paper towel for a minute. Then, the conjugate pads were placed on a finger rack to dry at 37° C. for 1 hour. Blocked conjugate pads were put in a plastic bag with desiccators and stored in a dry room. The OD10 gold-conjugated BB2 antibody was prepared by adding 10% Sucrose and 5% Trehalose to the conjugate. The gold-conjugated antibody was dispensed onto the conjugate pads by an automatic striper (Matrix 160, Kinematic Automation, Inc., Twain Harte, Calif., USA) at a dispensing rate of 10 μl/cm. The conjugate pads were dried at 37° C. for 1 hour, packed in a desiccated foil pouch, and stored in a dry room.

Test Strip Lamination and Cutting:

The nitrocellulose membrane striped with the test antibody and control goat anti-mouse antibody was laminated onto a vinyl backing card (G&L. Precision Die Cutting, San Jose, Calif., USA). A wick pad (30250, EMI Specialty Papers, Redding, Conn., USA) was placed on the top portion of the backing, overlapping the membrane by 2 mm. A 10 mm conjugate pad was overlapped onto the membrane by 2 mm. A sample pad (Surewick 0048 cellulose pad, Millipore, Darmstadt, Germany) was placed on top of the conjugate pad with a 15 mm overlap from the bottom of the backing card. Assembled cards were cut into 4 mm strips using a cutter (CM4000, Biodot, Irvine, Calif., USA).

Extraction of Test Swabs:

Swab samples were obtained from test sites having different levels of bed bug infestations, designated as levels of 0, 2, 3, 4, 5, 7, and 8, with level 0 having the lowest level (i.e., no bed bugs) and 8 the highest level. Swabs were extracted in 350 μl of extraction buffer for 1 minutes at room temperature in an Eppendorf tube. Three extraction buffers were tested: extraction buffer 1 contained 1× Tris-HCl (pH 7.6), 0.05% $NaN_3$, 0.1% BSA, and 0.1% Tween-20; extraction buffer 2 contained 1× Tris-HCl (pH 7.6), 0.05% $NaN_3$, 0.1% BSA, and 0.2% Tween-20; and extraction buffer 3 contained 1× Tris-HCl (pH 7.6), 0.05% $NaN_3$, 0.25% BSA, and 0.1% Tween-20, Serial dilutions of the swab extracts were performed from ½ to $1/4096$.

Assay Testing Method:

70 μl of extraction buffer (negative control) or bed bug swab sample in extraction buffer was pipeted onto the sample pad. The test line intensity was read at 15 minutes by eye.

Figure 2:
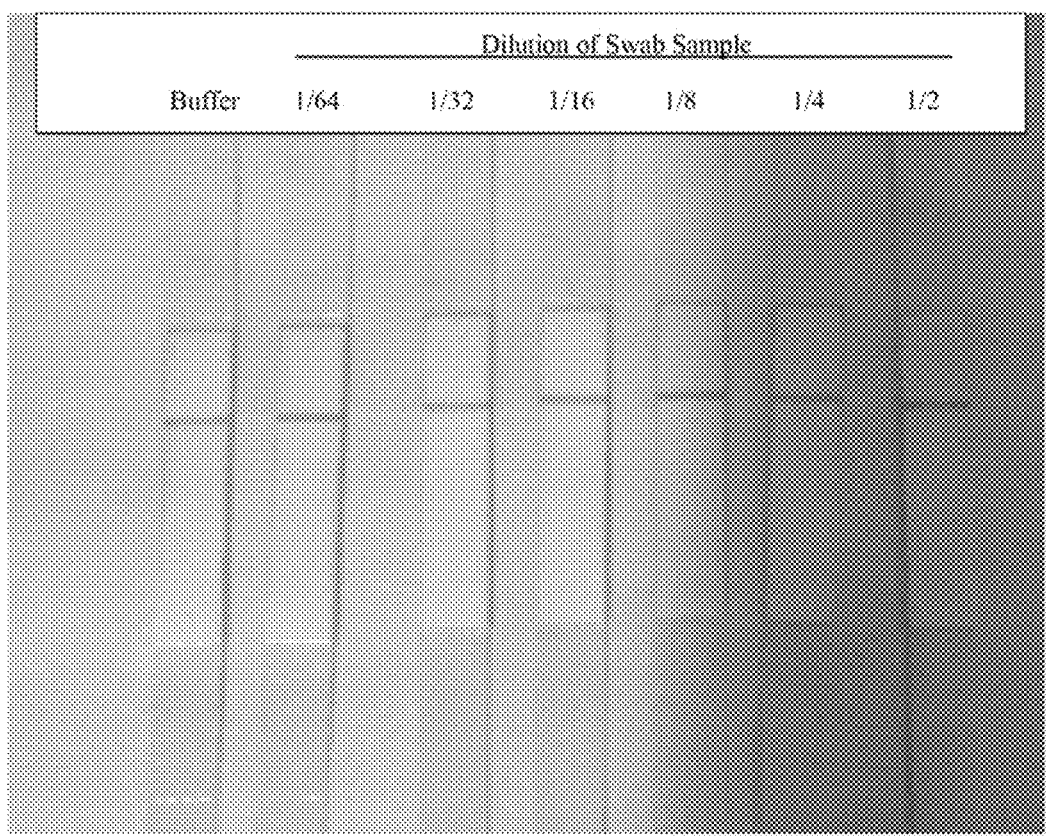
FIGS. 2-7 show the results of a lateral flow immunoassay for swab samples obtained from the noted levels of bed bug infestation, with level 0 containing no bed bugs and level 8 containing the highest level of bed bugs. Swab samples were extracted in extraction buffer 1 containing 1× Tris-HCl (pH 7.6), 0.05% NaN$_3$, 0.1% BSA, and 0.1% Tween-20 and the noted dilutions were applied to test strips. "Buffer" indicates a negative control test strip in which buffer 1 was applied instead of a swab sample. All of the strips contain a positive control stripe of goat anti-mouse antibody, which is located above a BB7 capture antibody stripe for binding bed bug antigen. The stripes become visually detectable only upon binding of the gold-conjugated mouse monoclonal BB2 antibody to the goat anti-mouse positive control stripe or to immobilized bed bug antigen captured by the BB7 stripe. The line on the "Buffer" strip and the corresponding lines on the test strips are the positive controls that indicate binding of the goat anti mouse antibody to the gold-conjugated BB2 detector antibody. Only positive controls are detectable in FIG. 2 due to the absence of antigen. The lines beneath the positive control lines in FIGS. 3-7 indicate binding of the gold-conjugated BB2 antibody to immobilized bed bug antigen captured by the 1387 stripe.
Figure 3:
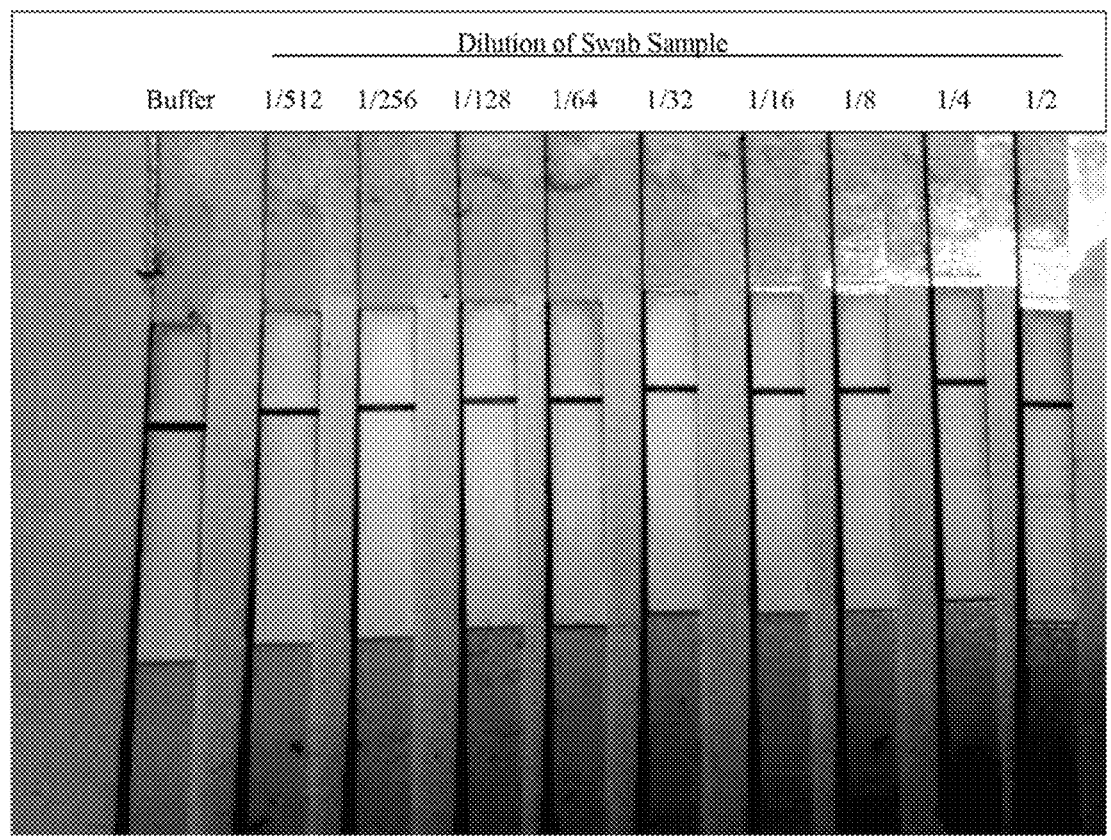
Figure 4:
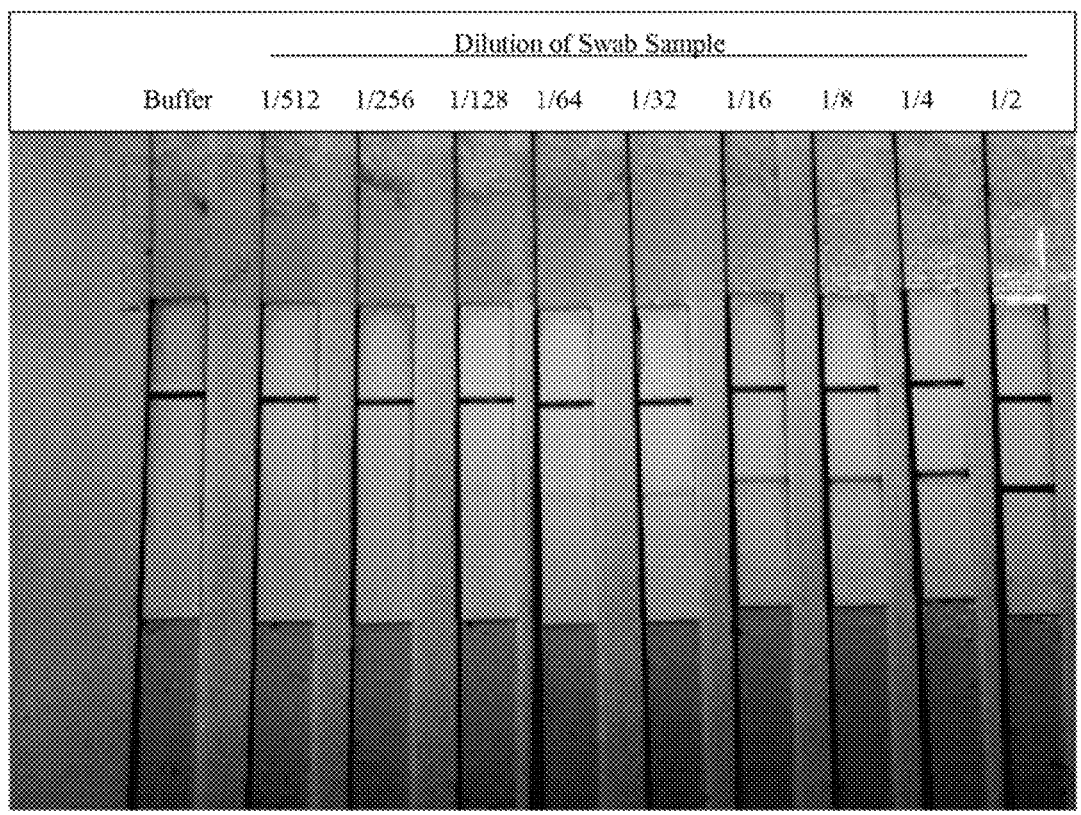
Figure 5:
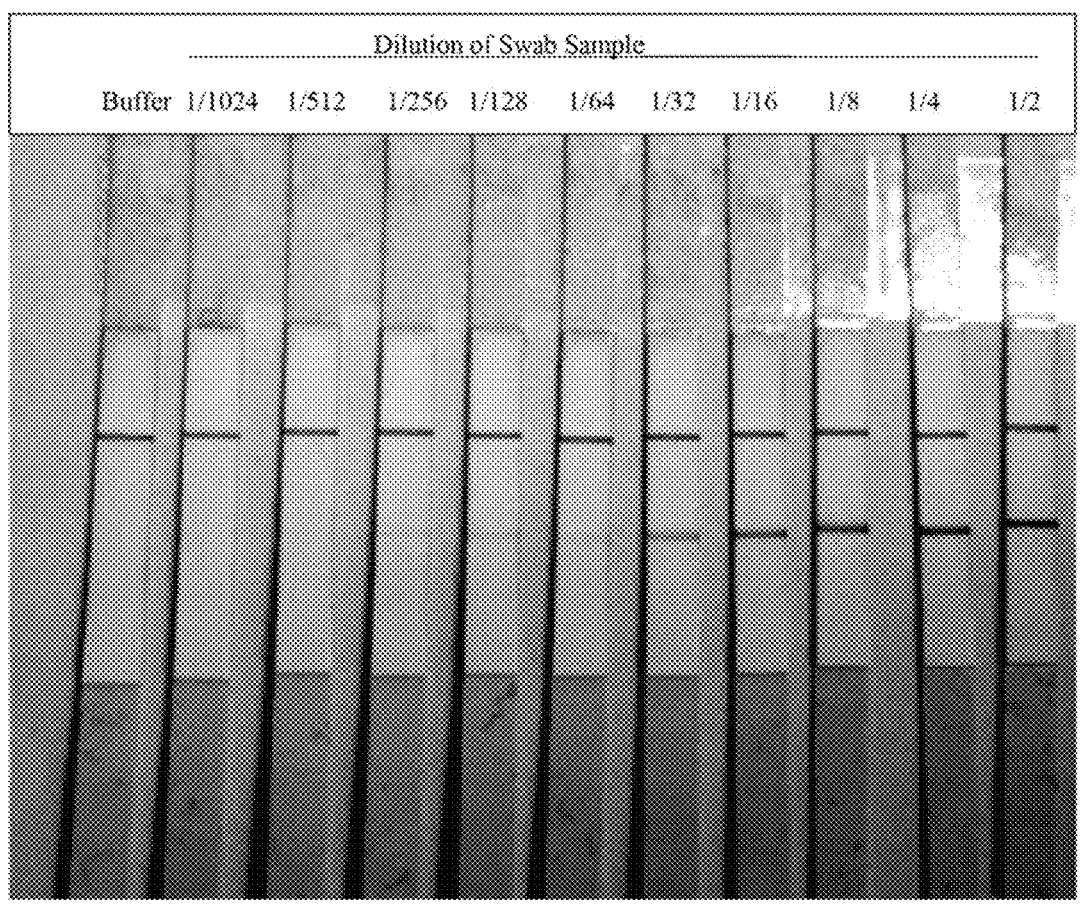
Figure 6:
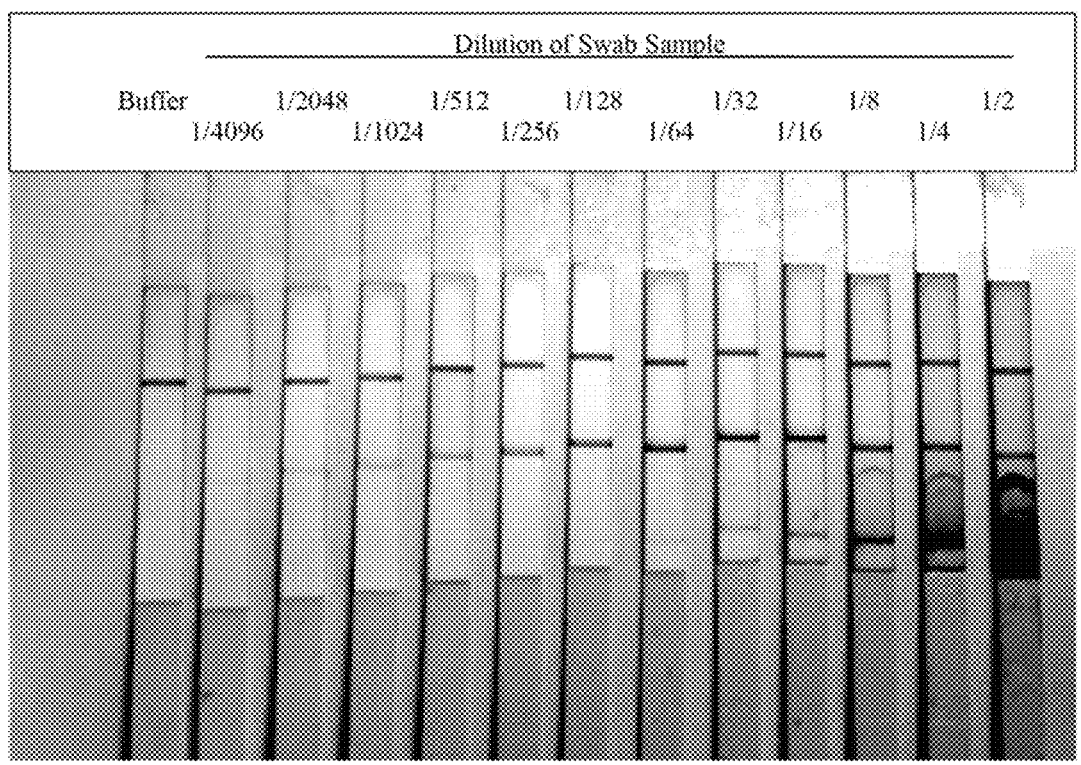
Figure 7:
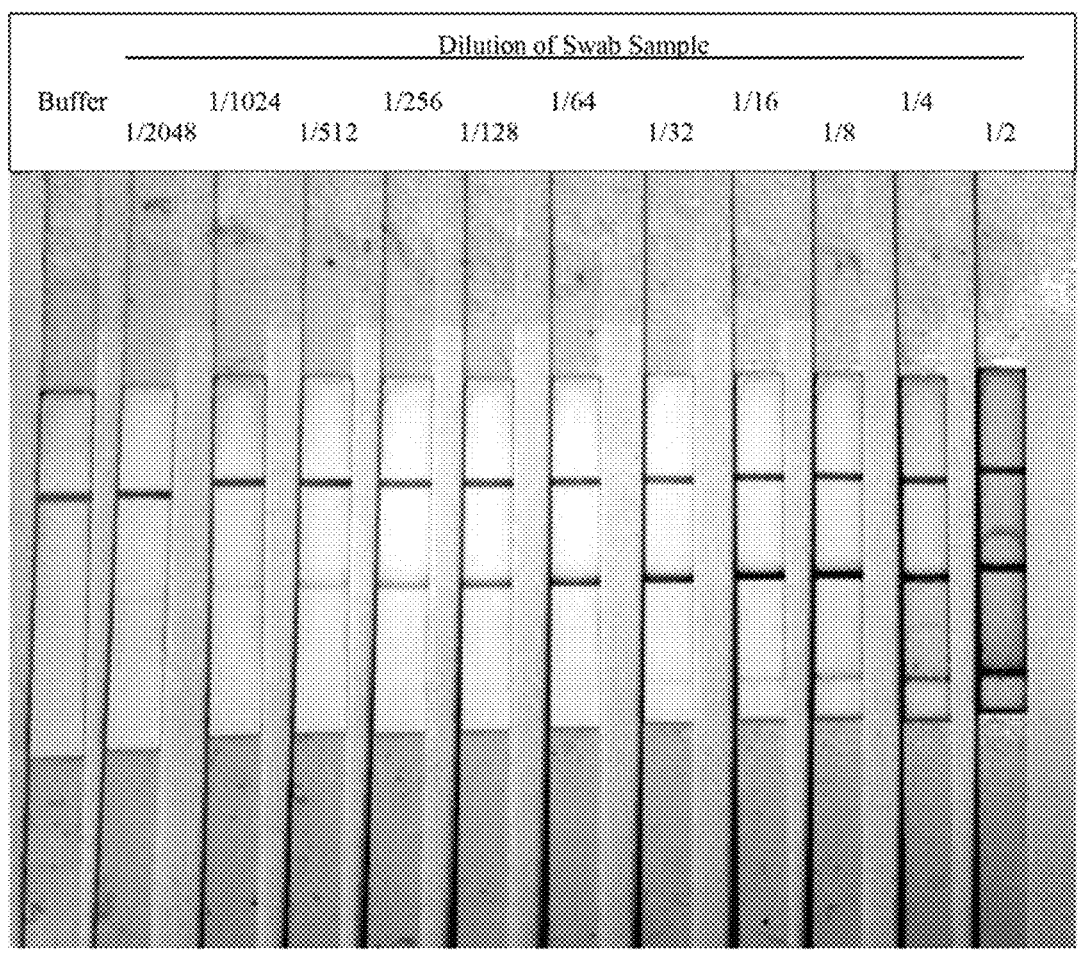

Extraction Buffer 1 Result:

As shown in FIGS. 2-7, all strips showed positive control lines for the binding of the goat anti-mouse antibody to the gold-conjugated BB2 antibody. All strips showed the absence of test lines for the negative control strip in which extraction buffer was added instead of a swab sample. FIG. 2 only shows positive control lines for the level 0 swab sample dilutions since bed bug antigen was not present. In FIGS. 3-7, the positive control lines are the top lines, and any test lines showing the presence of bed bug antigen are beneath the positive control lines. Dirt or insoluble particles from the swabs were present near the bottom of the membranes for level 3, 5, 7, and 5 test strips. The level 2 swab sample (FIG. 3) had visible test lines from the $1/16$ dilution to the ½ dilution. The level 3 swab sample (FIG. 4) had visible test lines from the $1/128$ dilution to the ½ dilution. The level 4 swab sample (FIG. 5) had visible test lines from the $1/1024$ dilution to the ½ dilution. The level 7 swab sample (FIG. 6) had visible test lines from the $1/4096$ dilution to the ½ dilution. The level 8 swab sample (FIG. 7) had visible test lines from the $1/2048$ dilution to the ½ dilution. Although visually observed, some of the noted test lines are not readily apparent for certain dilutions in FIGS. 3-7 due to photographic limitations. All test lines were without smears. The signal intensity of the ½ dilution from the level 2 swab was approximately equal to that of the $1/32$ dilution from the level 3 swab, the $1/64$ dilution front the level 4 swab, the $1/1024$ dilution from the level 7 swab, and the $1/512$ dilution from the level 8 swab. Therefore, visible signal intensity of the ½ dilution from the level 2 swab was weakest, compared to that of the ½ dilutions from the level 3, 4, 7 and 8 swabs. The signal of the ½ dilution from the level 8 swab was the strongest.

Signal intensities were also determined using an Axxin test strip reader (Axxin, Fairfield, Victoria, Australia) to measure the test line areas for different concentrations ($1/2048$ to ½) of level 0, 2, 3, 4, 7, and 8 swab samples extracted in 350 μl of buffer 1. The results are shown in Table 2.

TABLE 2

Test Line Areas from Different Concentrations of Swab Samples (Buffer 1)

| Concentration | Test Line Areas | | | | | |
|---|---|---|---|---|---|---|
| | Level 8 | Level 7 | Level 4 | Level 3 | Level 2 | Level 0 |
| 0 | 253 | 397 | 232 | 267 | 237 | 362 |
| $1/2048$ | 654 | 1187 | — | — | — | — |
| $1/1024$ | 1013 | 1978 | 359 | — | — | — |
| $1/512$ | 1936 | 3291 | 443 | 336 | 297 | — |
| $1/256$ | 3388 | 5356 | 681 | 526 | 284 | — |
| $1/128$ | 5373 | 7348 | 990 | 526 | 285 | — |
| $1/64$ | 7662 | 10522 | 840 | 743 | 326 | 327 |
| $1/32$ | 9341 | 11385 | 3024 | 1199 | 310 | 296 |
| $1/16$ | 11420 | 12550 | 4609 | 2095 | 411 | 265 |
| $1/8$ | 12066 | 8830 | 7500 | 3309 | 392 | 433 |
| $1/4$ | 9793 | 7765 | 7980 | 6161 | 574 | 316 |
| $1/2$ | 8693 | 6279 | 8550 | 8516 | 967 | 448 |

For each level, a reading was obtained for buffer as a negative control (i.e., concentration "0"). The negative control reading (Bo) was divided by itself to yield a normalized value of 1. The negative control reading (Bo) was then divided by the test line area (B) for each dilution in the level, where smaller values under 1 suggest larger amounts of bed bug antigen and values above 1 it absence of bed bug antigen. The data expressed as Bo/B is provided in Table 3.

TABLE 3

Bo/B Calculated from Test Line Areas from Different Concentrations of Swab Samples (Buffer 1)

| Concentration | Bo/B | | | | | |
|---|---|---|---|---|---|---|
| | Level 8 | Level 7 | Level 4 | Level 3 | Level 2 | Level 0 |
| 0 | 1 | 1 | 1 | 1 | 1 | 1 |
| [1/2048] | 0.3869 | 0.3345 | — | — | — | — |
| [1/1024] | 0.2498 | 0.2007 | 0.6462 | — | — | — |
| [1/512] | 0.1307 | 0.1206 | 0.5237 | 0.7946 | 0.798 | — |
| [1/256] | 0.0747 | 0.0741 | 0.3407 | 0.5076 | 0.8345 | — |
| [1/128] | 0.0471 | 0.054 | 0.2343 | 0.5076 | 0.8316 | — |
| [1/64] | 0.033 | 0.0377 | 0.2762 | 0.3594 | 0.727 | 1.107 |
| [1/32] | 0.0271 | 0.0349 | 0.0767 | 0.2227 | 0.7645 | 1.223 |
| [1/16] | 0.0222 | 0.0316 | 0.0503 | 0.1274 | 0.5766 | 1.366 |
| [1/8] | 0.021 | 0.045 | 0.0309 | 0.0807 | 0.6046 | 0.836 |
| [1/4] | 0.0258 | 0.0511 | 0.0291 | 0.0433 | 0.4129 | 1.146 |
| [1/2] | 0.0291 | 0.0632 | 0.0271 | 0.0314 | 0.2451 | 0.808 |

Figure 8A:
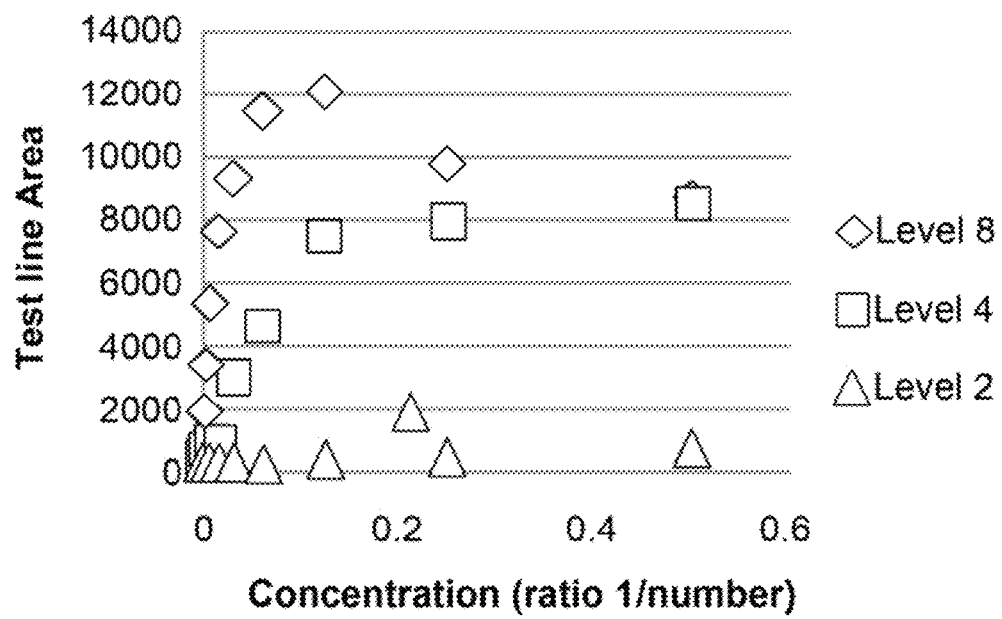
FIGS. 8A and 8B are graphs based on measurements made by the Axxin test strip reader of swab samples for levels 2, 4, and 8 extracted in buffer 1.
Figure 8B:
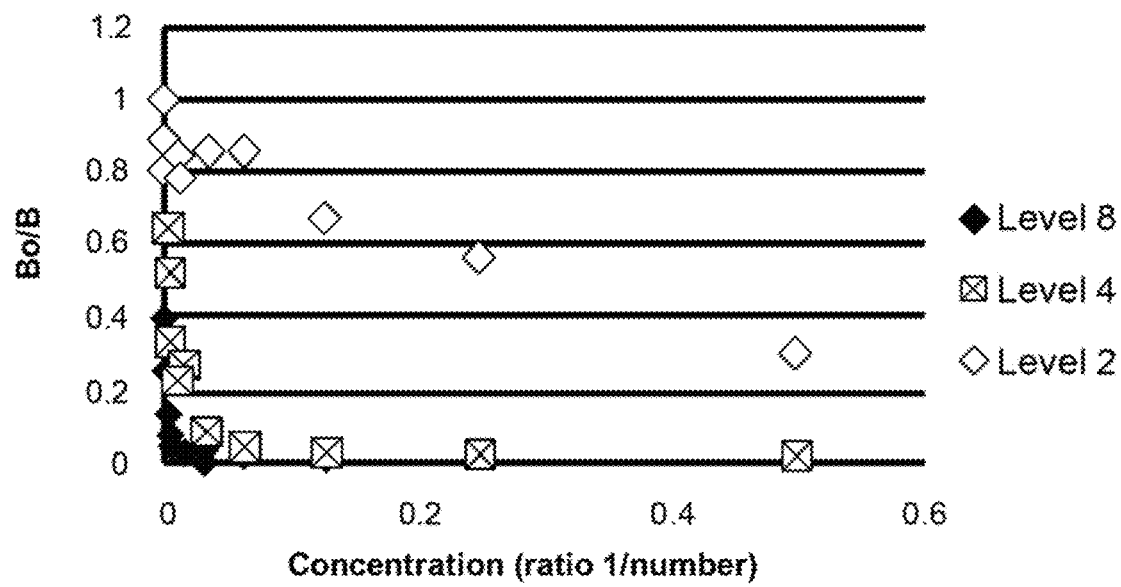

Tables 2-3 and FIG. 8A show, in general, that the measured values of concentrations from level 8 swabs (corresponding to the greatest level of bed bug infestation) were highest and values of concentrations from level 2 swabs (corresponding to the smallest level of bed bug infestation) were lowest. Table 2 and FIG. 8B show that level 8 swabs produced better signal intensities than level 2 and level 4 swabs. Table 3 suggests that level 8 swabs contained more bed bug antigen than other levels.

Figure 9:
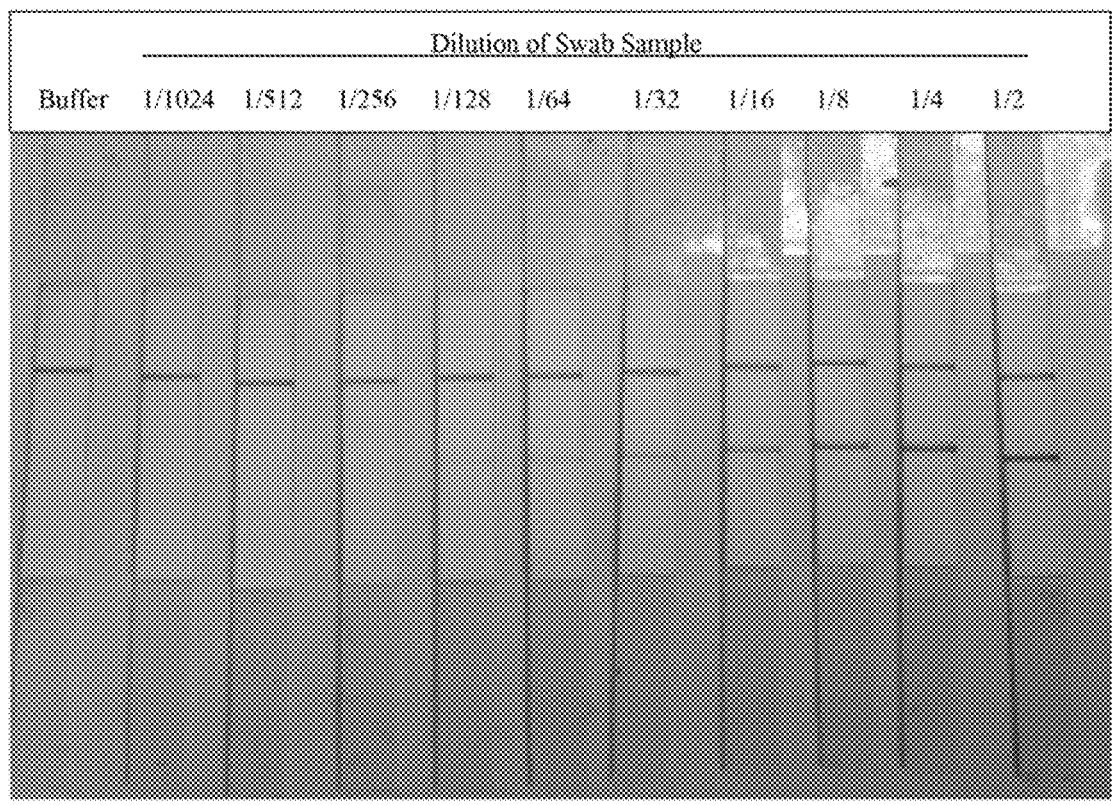
Figure 10:
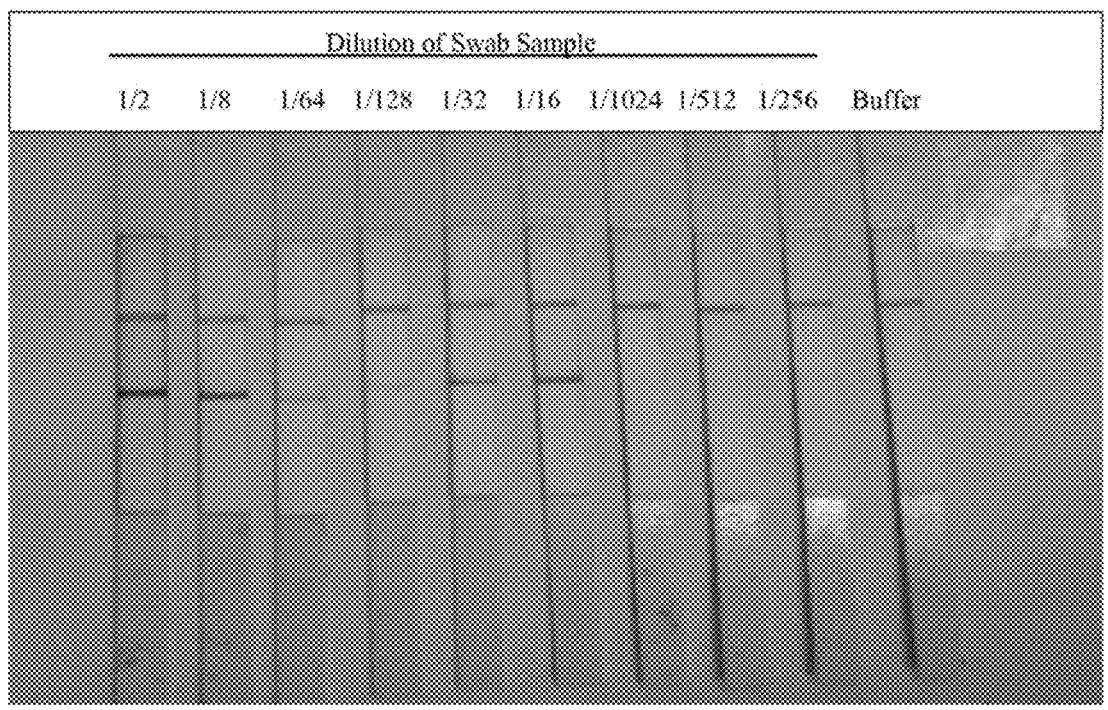

Extraction Buffer 2 Results:

As shown in FIGS. 9-11, all strips showed positive control lines for the binding of the goat anti-mouse antibody to the gold-conjugated BB2 antibody. All strips showed the absence of test lines for the negative control strip in which extraction buffer was added instead of a swab sample, in FIGS. 9-11, the positive control lines are the top lines, and any test lines showing the presence of bed bug antigen are beneath the positive control lines. Dirt or insoluble particles from the swabs were present near the bottom of the membranes for level 4, 5, and 8 test strips. The level 4 swab sample (FIG. 9) had visible test lines from the 1/512 dilution to the 1/2 dilution. The level 5 and 8 swab samples (FIGS. 10 and 11, respectively) had visible test lines from the 1/1024 dilution to the 1/2 dilution. Although visually observed, some of the noted test lines are not readily apparent for certain dilutions in FIGS. 9-11 due to photographic limitations. All test lines were smeared. The signal intensity of the 1/16 dilution from the level 4 swab was approximately equal to that of the 1/64 dilution from the level 5 and 8 swabs. Signal intensity was weakest for the level 4 swab and similar between the level 5 and 8 swabs.

Signal intensities were also determined using an Axxin test strip reader (Axxin, Fairfield, Victoria, Australia) to measure the test line areas for different concentrations (1/2048 to 1/2) of level 4, 5, and 8 swab samples extracted in 350 µl of buffer 2. The results are shown in Table 4.

TABLE 4

Test Line Areas from Different Concentrations of Swab Samples (Buffer 2)

| | Test Line Areas | | |
|---|---|---|---|
| Concentration | Level 8 | Level 5 | Level 4 |
| 0 | 195 | 230 | 217 |
| 1/2048 | 365 | — | — |
| 1/1024 | 693 | 542 | 356 |

TABLE 4-continued

Test Line Areas from Different Concentrations of Swab Samples (Buffer 2)

| | Test Line Areas | | |
|---|---|---|---|
| Concentration | Level 8 | Level 5 | Level 4 |
| 1/512 | 961 | 810 | 446 |
| 1/256 | 1787 | 1395 | 527 |
| 1/128 | 3250 | 2143 | 959 |
| 1/64 | 5225 | 4157 | 1623 |
| 1/32 | 7927 | 6696 | 2692 |
| 1/16 | 9306 | 9766 | 4413 |
| 1/8 | 10647 | 10173 | 6685 |
| 1/4 | 11489 | — | 8605 |
| 1/2 | 9818 | 12250 | 10150 |

The data expressed as Bo/B calculated from test line areas is provided in Table 5.

TABLE 5

Bo/B Calculated from Test Line Areas from Different Concentrations of Swab Samples (Buffer 2)

| | Bo/B | | |
|---|---|---|---|
| Concentration | Level 8 | Level 5 | Level 4 |
| 0 | 1 | 1 | 1 |
| [1/2048] | 0.5342 | — | — |
| [1/1024] | 0.2814 | 0.4244 | 0.6096 |
| [1/512] | 0.2029 | 0.2840 | 0.4865 |
| [1/256] | 0.1091 | 0.1649 | 0.4118 |
| [1/128] | 0.06 | 0.1073 | 0.2263 |
| [1/64] | 0.0373 | 0.0553 | 0.1337 |
| [1/32] | 0.0246 | 0.0343 | 0.0806 |
| [1/16] | 0.0210 | 0.0236 | 0.0492 |
| [1/8] | 0.0183 | 0.0226 | 0.0325 |
| [1/4] | 0.0170 | — | 0.0252 |
| [1/2] | 0.0199 | 0.0188 | 0.0214 |

Figure 12A:
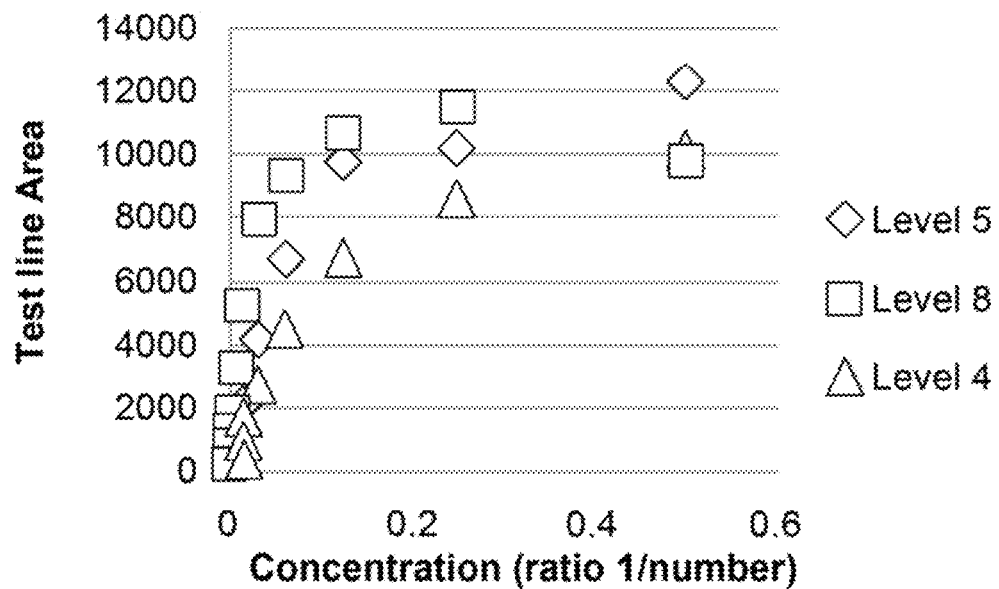
FIGS. 12A and 12B are graphs based on measurements made by the Axxin test strip reader of swab samples for levels 4, 5, and 8 extracted in buffer 2. Labeling of the graphs is as described for FIGS. 8A and 8B.
Figure 12B:
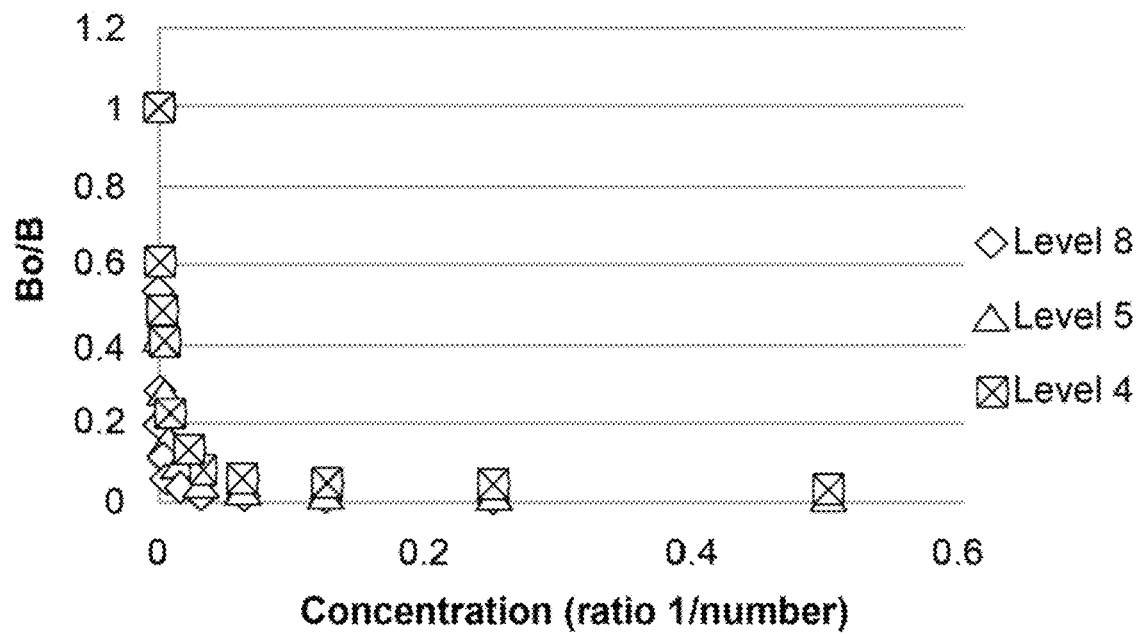
Figure 14:
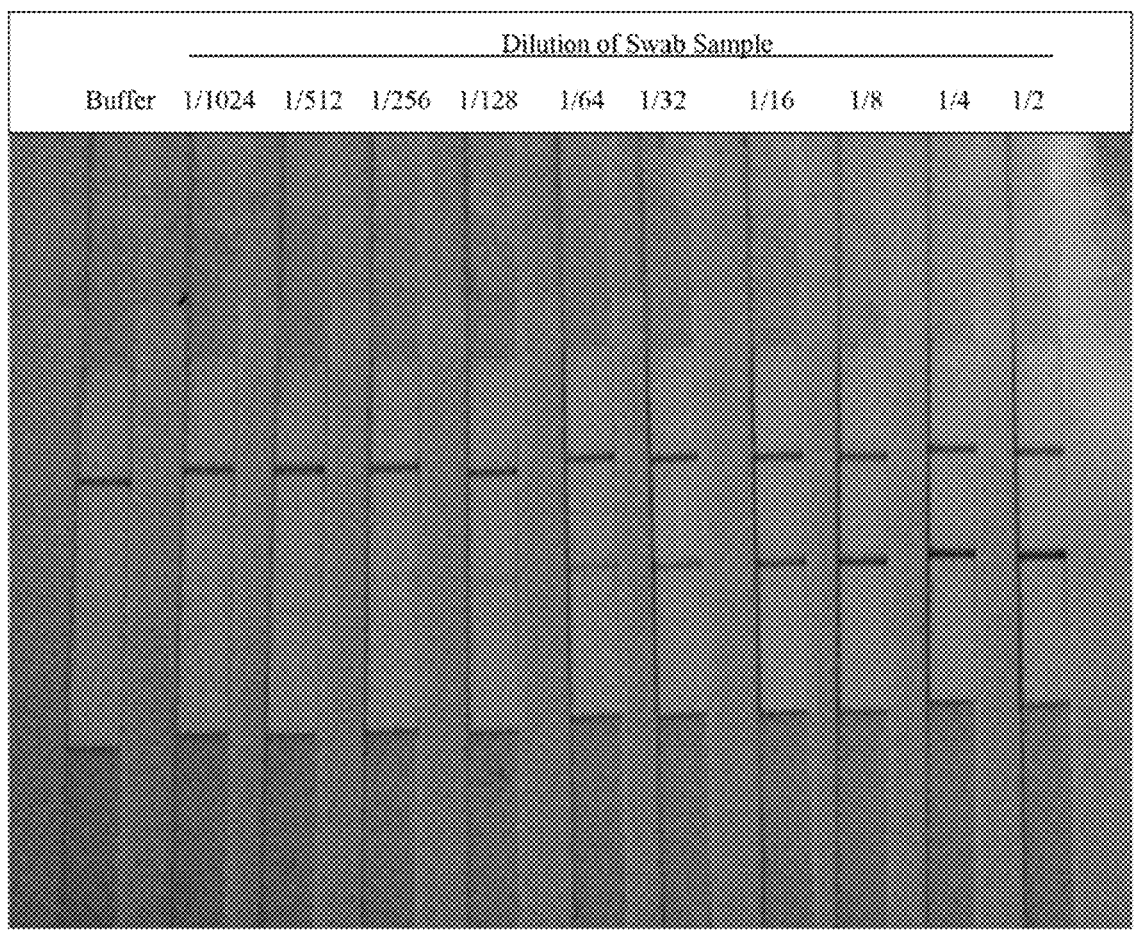
Figure 15:
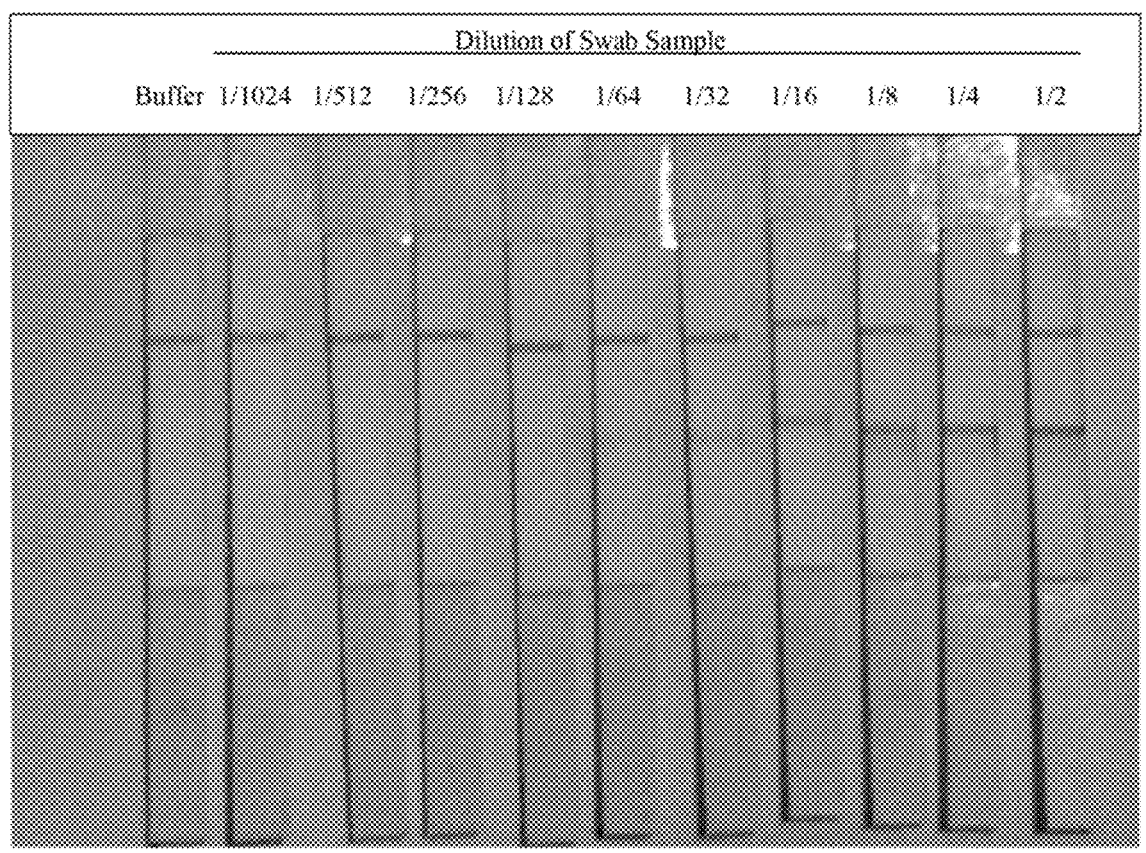
Figure 17:
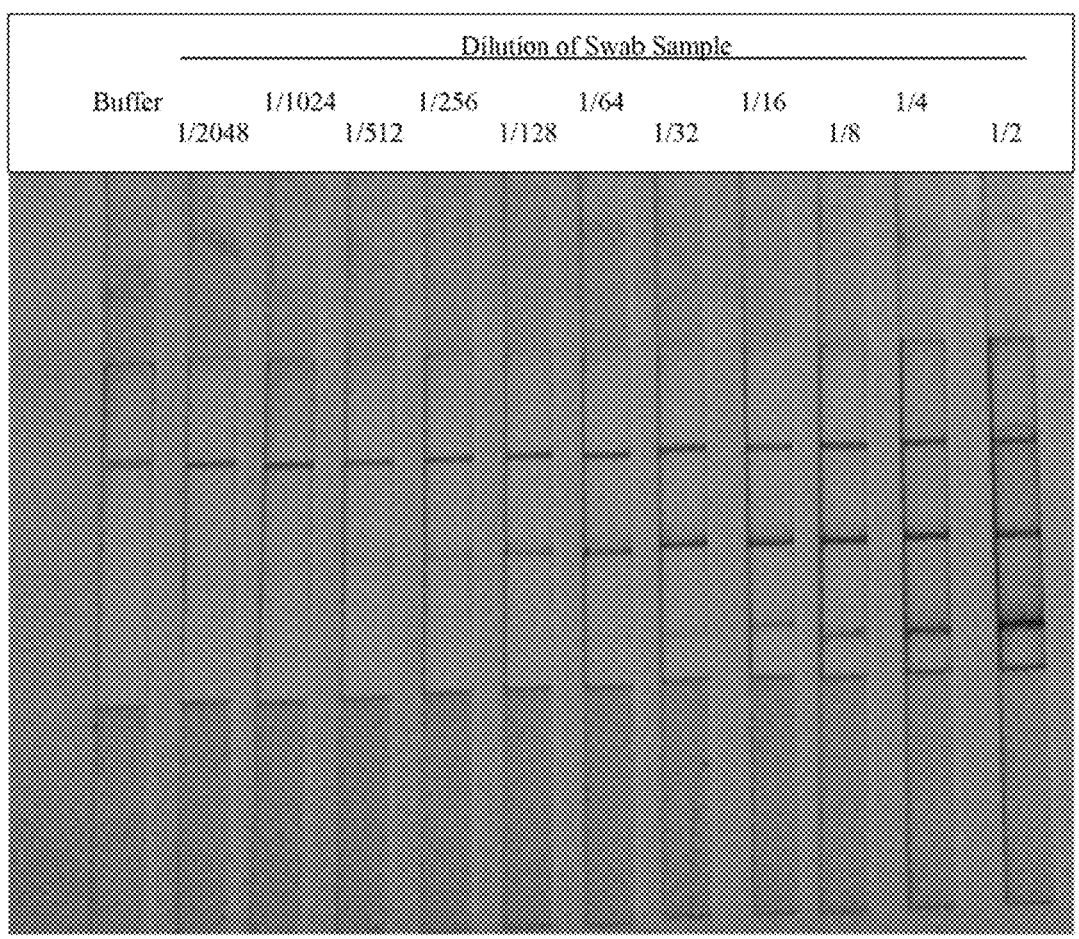

Tables 4-5 and FIG. 12A show that, in general, measured values of level 8 swabs were the highest and values of level 4 swabs were the lowest. Although visibility of test lines from level 5 swabs were similar to level 8 swabs (FIGS. 10 and 11, respectively), Axxin reader results in Table 4 and FIG. 12A show that level 8 swabs produced better signal intensities than level 4 and 5 swabs. Table 5 suggests that level 8 swabs contained more bed bug antigen than the other levels.

Extraction Buffer 3 Results:

As shown in FIGS. 13-17, all strips showed positive control lines for the binding of the goat anti-mouse antibody to the gold-conjugated BB2 antibody. All strips showed the absence of test lines for the negative control strip in which extraction buffer was added instead of a swab sample. In FIGS. 13-17, the positive control lines are the top lines, and any test lines showing the presence of bed bug antigen are beneath the positive control lines. Dirt or insoluble particles from the swabs were present near the bottom of the membranes for level 3, 5, 7, and 8 test strips. The level 2 swab sample (not shown) had visible test lines from the 1/8 dilution to the 1/2 dilution. The level 3 swab sample (FIG. 13) had visible test lines from the 1/128 dilution to the 1/2 dilution. The level 4 swab sample (FIG. 14) had visible test lines from the 1/1024 dilution to the 1/2 dilution. The level 5 swab sample (FIG. 15) had visible test lines from the 1/512 dilution to the 1/2 dilution. The level 7 swab sample (FIG. 16) had visible test lines from the 1/4096 dilution to the 1/2 dilution. The level 8 swab sample (FIG. 17) had visible test lines from the 1/2048 dilution to the ½ dilution. Although visually observed, some of the noted test lines are not readily apparent for certain dilutions in FIGS. 13-17 due to photographic limitations. All test lines were smeared. The signal intensity of the ½ dilution from the level 2 swab was approximately equal to that of the 1/64 dilution from the level 3 swab, the 1/64 dilution from the level 4 swab, the 1/64 dilution from the level 5 swab, the 1/1024 dilution from the level 7 swab, and the 1/512 dilution from the level 8 swab. Therefore, visible signal intensity of the ½ dilution from the level 2 swab was weakest compared to that of the ½ dilutions from the other levels. The signal of the ½ dilution from the level 8 swab was the strongest.

Signal intensities were also determined using an Axxin test strip reader (Axxin, Fairfield, Victoria, Australia) to measure the test line areas for different concentrations (1/2048 to ½) of level 4, 5, and 8 swab samples extracted in 350 µl of buffer 3. The results are shown in Table 6.

TABLE 6

Test Line Areas from Different Concentrations of Swab Samples (Buffer 3)

| | Test Line Areas | | | | | |
|---|---|---|---|---|---|---|
| Concentration | Level 8 | Level 7 | Level 5 | Level 4 | Level 3 | Level 2 |
| 0 | 441 | 283 | 263 | 225 | 170 | 231 |
| 1/2048 | 735 | 781 | — | — | — | — |
| 1/1024 | 798 | 1037 | 270 | 334 | — | — |
| 1/512 | 1414 | 2003 | 385 | 574 | 309 | 261 |
| 1/256 | 2691 | 2998 | 422 | 1090 | 403 | 261 |
| 1/128 | 4741 | 4665 | 1026 | 1439 | 522 | 285 |
| 1/64 | 7173 | 6912 | 2013 | 2403 | 724 | 276 |
| 1/32 | 9603 | 8746 | 5763 | 4090 | 1360 | 269 |
| 1/16 | 10377 | 9626 | 5743 | 5842 | 2430 | 271 |
| 1/8 | 11788 | 11767 | 7021 | 8061 | 3462 | 340 |
| 1/4 | 10725 | 8466 | 7120 | 9518 | 5189 | 406 |
| 1/2 | 8584 | 6803 | 9408 | 10413 | 6098 | 752 |

The data expressed as Bo/B calculated from test line areas is provided in Table 7.

TABLE 7

Bo/B Calculated from Test Line Areas from Different Concentrations of Swab Samples (Buffer 3)

| | Bo/B | | | | | |
|---|---|---|---|---|---|---|
| Concentration | Level 8 | Level 7 | Level 5 | Level 4 | Level 3 | Level 2 |
| 0 | 1 | 1 | 1 | 1 | 1 | 1 |
| [1/2048] | 0.6 | 0.3624 | — | — | — | — |
| [1/1024] | 0.5526 | 0.2729 | 0.9741 | 0.6737 | — | — |
| [1/512] | 0.3119 | 0.1413 | 0.6831 | 0.3920 | 0.5502 | 0.8851 |
| [1/256] | 0.1639 | 0.0944 | 0.6232 | 0.2064 | 0.4218 | 0.8851 |
| [1/128] | 0.0930 | 0.0607 | 0.2563 | 0.1564 | 0.3257 | 0.8105 |
| [1/64] | 0.0615 | 0.0409 | 0.1307 | 0.0936 | 0.2348 | 0.8370 |
| [1/32] | 0.0459 | 0.0324 | 0.0456 | 0.0550 | 0.1250 | 0.8587 |
| [1/16] | 0.0425 | 0.0294 | 0.0458 | 0.0385 | 0.0700 | 0.8524 |
| [1/8] | 0.0374 | 0.0241 | 0.0375 | 0.0279 | 0.0491 | 0.6794 |
| [1/4] | 0.0411 | 0.0334 | 0.0369 | 0.0236 | 0.0328 | 0.5690 |
| [1/2] | 0.0514 | 0.0416 | 0.0280 | 0.0216 | 0.0279 | 0.3072 |

Figure 18A:
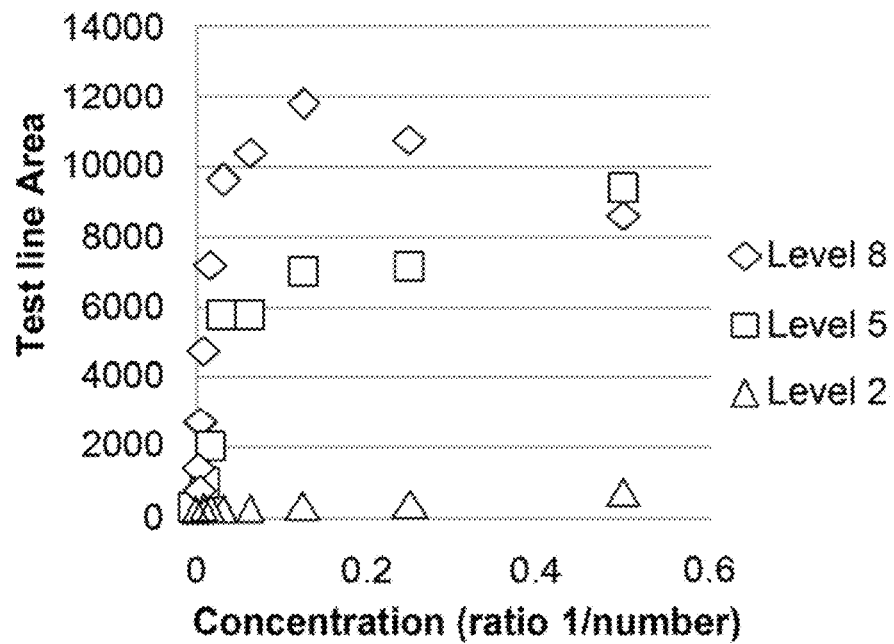
FIGS. 18A and 18B are graphs based on measurements made by the Axxin test strip reader of swab samples for levels 2, 5, and 8 extracted in buffer 3. Labeling of the graphs is as described for FIGS. 8A and 8B.
Figure 18B:
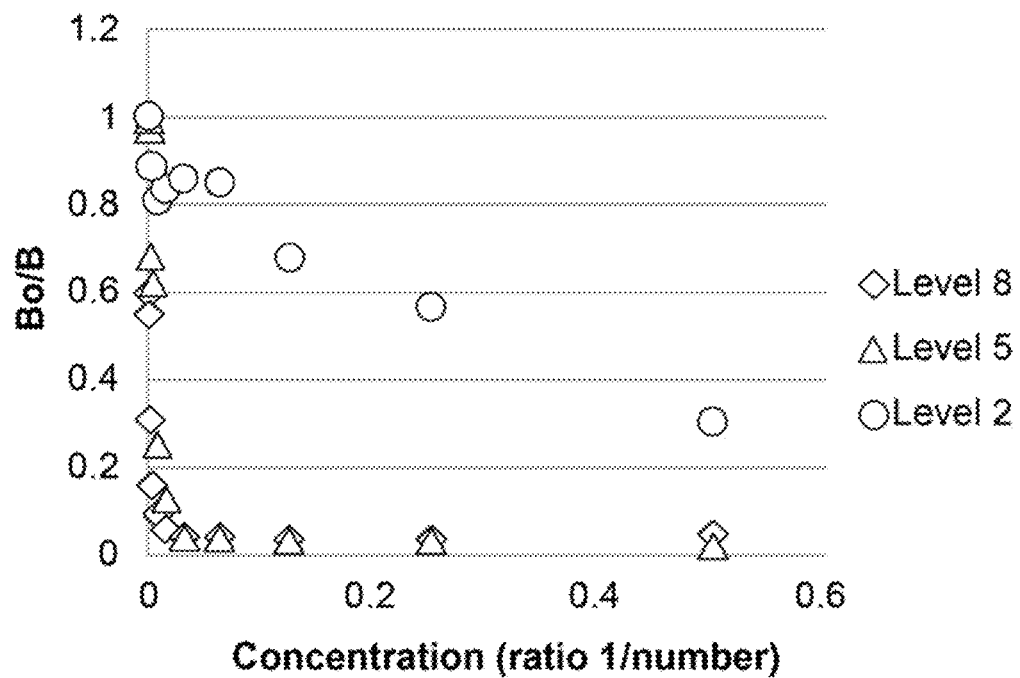
Figure 19A:
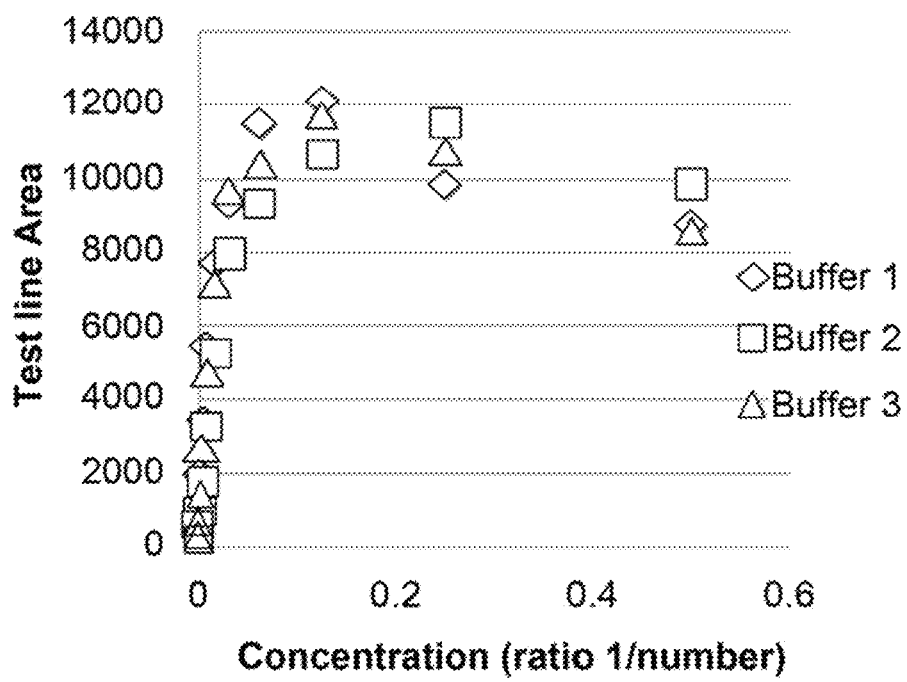
FIGS. 19A and 19B are graphs based on measurements made by the Axxin test strip reader showing a comparison of results for level 8 swab samples extracted in buffers 1, 2, and 3. Labeling of the graphs is as described for FIGS. 8A and 8B.
Figure 19B:
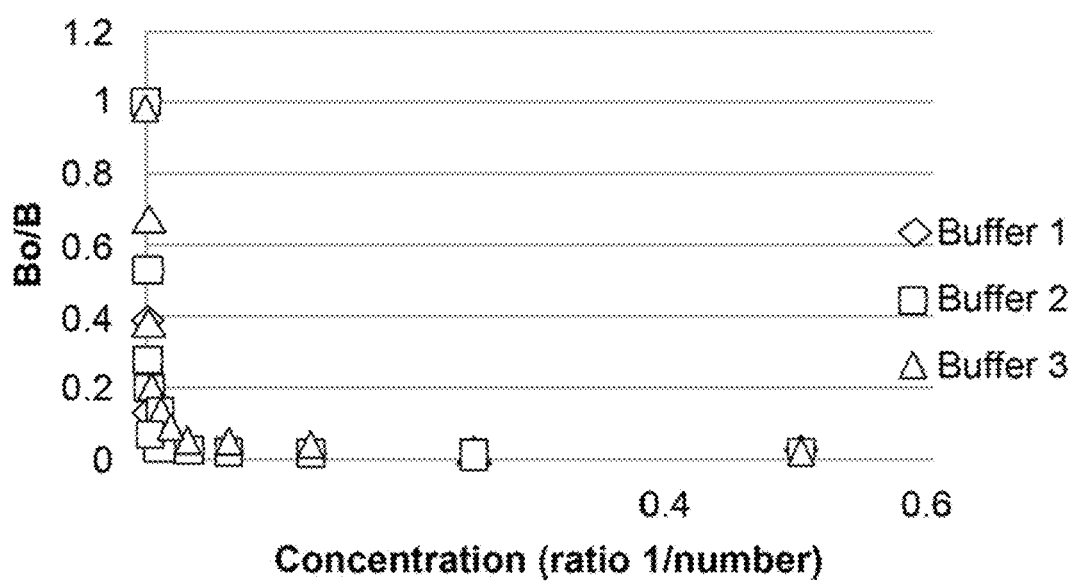

Tables 6-7 and FIG. 18A show that, in general, measured values of level 8 swabs were highest and values of level 2 swabs were lowest. Table 7 and FIG. 18A show that level 8 swabs produced better signal intensities than the other levels.

Comparison of Extraction Buffers:

For extraction buffer 1, all test lines were clear and did not have smears, while extraction buffers 2 and 3 resulted in smeared test lines. For level 4 swabs, extraction with buffers 1 and 3 resulted in signals starting at the 1/1024 dilution, but extraction with buffer 2 resulted in signals starting at the 1/512 dilution. However, extraction of level 5 with buffer 2 yielded signal at a lower concentration (1/1024 dilution) than extraction with buffer 3 (1/512 dilution). Buffers 1 and 3 yielded signals at the same concentration for level 3 and 7 swabs. However, extraction of level 2 swabs with buffer 1 resulted in a signal at, a lower concentration (1/16 dilution) than extraction with buffer 3 (1/8 dilution). In general, measured values of all test level swabs were higher for extraction with buffer 1 than for buffers 2 and 3.

Figure 20:
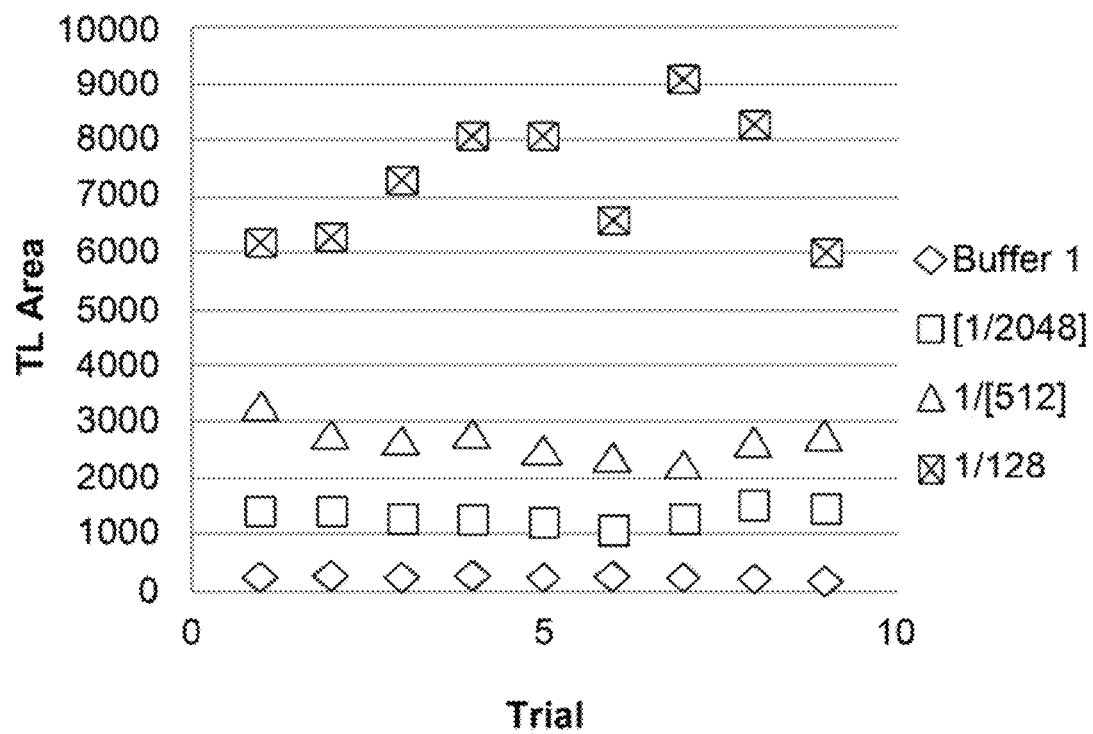
FIG. 20 is a graph based on measurements made by the Axxin test strip reader for nine replicates of extraction buffer 1 as a negative control and nine replicates each of 1/2048, 1/512, and 1/128 dilutions for level 7 swab samples extracted in buffer 1. The x-axis indicates the nine replicates by "trial" number; the y-axis is as described for FIG. 8A.

Precision Study Using Axxin Reader:

Nine replicates of extraction buffer 1 as a negative control and nine replicates each of 1/2048, 1/512, and 1/128 dilutions of level 7 swabs extracted with buffer 1 were prepared and test line areas were measured using an Axxin test strip reader (Axxin, Fairfield, Victoria, Australia). Test line areas are shown in Table 8 and FIG. 20.

TABLE 8

Precision Study Results of Replicate Test Line Areas

| | | Test Line Areas | | |
|---|---|---|---|---|
| Trial | Buffer 1 | Level 7 1/2048 | Level 7 1/512 | Level 7 1/128 |
| 1 | 250 | 1415 | 3299 | 6163 |
| 2 | 251 | 1426 | 2794 | 6276 |
| 3 | 233 | 1293 | 2684 | 7305 |
| 4 | 289 | 1238 | 2810 | 8079 |
| 5 | 260 | 1202 | 2531 | 8090 |
| 6 | 271 | 1075 | 2401 | 6583 |
| 7 | 260 | 1283 | 2260 | 9109 |
| 8 | 218 | 1540 | 2660 | 8297 |
| 9 | 194 | 1444 | 2773 | 5997 |
| Average | 247.3 | 1324.0 | 2690.2 | 7322.1 |
| STDEV | 28.6 | 144.3 | 295.3 | 1120.6 |
| % CV | 11.6 | 10.9 | 11.0 | 15.3 |

The percent coefficient of variation (% CV) was less than 20%, which is a good % CV for Axxin measurements.

The invention is not to be limited in scope by the specific embodiments described herein, indeed, various modifications of the invention in addition to those described will become apparent to those skilled in the art from the foregoing description and accompanying figures. Such modifications are intended to fall within the scope of the appended claims.

All references (e.g., publications or patents or patent applications) cited herein are incorporated herein by reference in their entirety and for all purposes to the same extent as if each individual reference (e.g., publication or patent or patent application) was specifically and individually indicated to be incorporated by reference in its entirety for all purposes.

Other embodiments are within the following claims.

What is claimed:

1. An antibody produced by a hybridoma deposited at the American Type Culture Collection (ATCC) under Accession Number PTA-122644 [BB2] or PTA-122645 [BB7], or an antigen-binding fragment thereof.

2. A monoclonal antibody or an antigen-binding fragment thereof comprising the three heavy and three light chain complementarity determining regions of the antibody of claim 1.

3. The antibody or antigen-binding fragment of claim 2, comprising the heavy and light chain variable regions of the antibody of claim 1.

4. The antibody or antigen-binding fragment of claim 3, comprising the heavy and light chains of the antibody of claim 1.

5. The antibody or antigen-binding fragment of claim 1, wherein the antibody or antigen-binding fragment is capable of binding to a bed bug antigen in a lysate of whole bed bugs or an extract of collection paper comprising bed bug waste material.

6. A conjugated monoclonal antibody or conjugated antigen-binding fragment, comprising the antibody or antigen-binding fragment of claim 1 and a detection agent.

7. The conjugated antibody or conjugated antigen-binding fragment of claim 6, wherein the detection agent is colloidal gold.

8. The conjugated antibody or conjugated antigen-binding fragment of claim 6, comprising the antibody produced by the hybridoma deposited at the ATCC under Accession Number PTA-122644 [BB2], or an antigen binding fragment thereof.

9. The conjugated antibody or conjugated antigen-binding fragment of claim 6, comprising the antibody produced by the hybridoma deposited at the ATCC under Accession Number PTA-122645 [BB7], or an antigen binding fragment thereof.

10. A composition comprising the antibody or antigen-binding fragment of claim 1.

11. A composition comprising:
(a) an antibody produced by a hybridoma deposited at the American Type Culture Collection (ATCC) under Accession Number PTA-122644 [BB2], and
(b) an antibody produced by a hybridoma deposited at the American Type Culture Collection (ATCC) under Accession Number PTA-122645 [BB7], or the conjugated antibody of claim 9.

12. A composition comprising:
(a) an antibody produced by a hybridoma deposited at the American Type Culture Collection (ATCC) under Accession Number PTA-122645 [BB7], and
(b) an antibody produced by a hybridoma deposited at the American Type Culture Collection (ATCC) under Accession Number PTA-122644 [BB2], or the conjugated antibody of claim 8.

13. A kit comprising the antibody or antigen-binding fragment of claim 1.

14. A hybridoma capable of producing an antibody, wherein the hybridoma is deposited at the ATCC under Accession Number PTA-122644 [BB2] or PTA-122645 [BB7].

15. An isolated cell producing the antibody or antigen-binding fragment of claim 1.

16. A method of making the antibody or antigen-binding fragment of claim 1, comprising (a) culturing a cell that produces the antibody or antigen-binding fragment, and (b) isolating the antibody or antigen-binding fragment from the cultured cell.

17. A method of detecting bed bugs, comprising contacting a sample comprising a bed bug antigen with the antibody or antigen-binding fragment of claim 1, and detecting binding of the bed bug antigen to the antibody or antigen-binding fragment.

18. The method of claim 17, wherein the detecting comprises performing a lateral flow assay.

19. The method of claim 17, wherein the method further comprises collecting the sample comprising the bed bug antigen with a collection device and extracting antigens from the sample.

20. The method of claim 19, wherein the collection device is a swab.

21. A method of detecting bed bugs, comprising contacting a sample comprising a bed bug antigen with an antibody produced by a hybridoma deposited at the American Type Culture Collection (ATCC) under Accession Number PTA-122644 [BB2], and the conjugated antibody of claim 9.

22. A method of detecting bed bugs, comprising contacting a sample comprising a bed bug antigen with an antibody produced by a hybridoma deposited at the American Type Culture Collection (ATCC) under Accession Number PTA-122645 [BB7], and the conjugated antibody of claim 8.

* * * * *